(12) United States Patent
Uang et al.

(10) Patent No.: US 8,609,839 B2
(45) Date of Patent: Dec. 17, 2013

(54) CAMPHOR-DERIVED COMPOUNDS, METHOD FOR MANUFACTURING THE SAME, AND APPLICATION THEREOF

(75) Inventors: Biing-Jiun Uang, Hsinchu (TW); Bo-Yao Yang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 31 days.

(21) Appl. No.: 13/009,677

(22) Filed: Jan. 19, 2011

(65) Prior Publication Data

US 2012/0077976 A1 Mar. 29, 2012

(30) Foreign Application Priority Data

Sep. 29, 2010 (TW) ............................... 99133061 A

(51) Int. Cl.
| | | |
|---|---|---|
| C07D 207/48 | (2006.01) | |
| C07D 213/89 | (2006.01) | |
| C07D 211/96 | (2006.01) | |
| C07D 233/42 | (2006.01) | |
| C07D 239/04 | (2006.01) | |
| C07D 233/02 | (2006.01) | |
| C07D 241/04 | (2006.01) | |
| C07D 295/26 | (2006.01) | |
| C07D 263/04 | (2006.01) | |
| C07D 265/04 | (2006.01) | |
| C07D 265/30 | (2006.01) | |
| C07D 277/04 | (2006.01) | |
| C07D 279/06 | (2006.01) | |
| C07D 279/12 | (2006.01) | |

(52) U.S. Cl.
USPC ........... 544/158; 544/242; 546/206; 548/542; 548/146; 548/215; 548/300.1; 564/80

(58) Field of Classification Search
USPC .............. 544/173; 546/206; 548/579; 564/80
See application file for complete search history.

(56) References Cited

U.S. PATENT DOCUMENTS 6,639,095 B1 * 10/2003 Uang et al. ...................... 560/55

FOREIGN PATENT DOCUMENTS

JP 11-012247 1/1999

OTHER PUBLICATIONS

Ramon, et al., Tetrahedron: Asymmetry, vol. 8, No. 14, pp. 2479-2496 (1997).*
Chen, et al., J. Org. Chem., 66:3650 (2001).*
M. Marzi et al., "Efficient Enantioselective Synthesis of (R)-(−)-Carnitine from Glycerol," J. Org. Chem., 2000, 65, pp. 6766-6769.
A.G.M. Barrett et al., "Diastereoselective Conjugate Addition to (+)-Camphorsulfonic Acid Derivative Nitroalkenes: Synthesis of α-Hydroxy and α-Amino Acids," J. Org. Chem., 1998, 63, pp. 5818-5823.
W. Oppolzer et al., "Asymmetric Diels-Alder Reactions: Facile Preparation and Structure of Sulfonamido-Isobornyl Acrylates," Tetrahedron Letters, vol. 25, No. 51, 1984, pp. 5885-5888.
D.J. Ramon et al., "Camphorsulfonamide derivatives: a new class of chiral catalysts for the titanium alkoxide-promoted addition of dialkylzinc to aldehydes," Tetrahedron: Asymmetry, vol. 8, No. 14, 1997, pp. 2479-2496.
X. Wang et al., "Catalytic cyanosilylaton of ketones with simple phosphonium salt," Tetrahedron Letters, 48, 2007, pp. 6010-6013.
B.E, Evans et al., "Nanomolar-Affinity, Non-Peptide Oxytocin Receptor Antagonists," J. Med. Chem., 36, 1993, pp. 3993-4005.

* cited by examiner

*Primary Examiner* — Michael Barker
(74) *Attorney, Agent, or Firm* — Muncy, Geissler, Olds & Lowe, PLLC

(57) ABSTRACT

Camphor-derived compounds are disclosed, which are represented as the following formula (I):

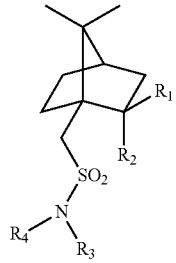

Formula (I)

wherein $R_1$, $R_2$, $R_3$, and $R_4$ each are defined as described in the specification. In addition, a method for manufacturing the camphor-derived compounds and application thereof are disclosed.

19 Claims, No Drawings

CAMPHOR-DERIVED COMPOUNDS, METHOD FOR MANUFACTURING THE SAME, AND APPLICATION THEREOF

BACKGROUND OF THE INVENTION

1. Field of the Invention

The present invention relates to a camphor-derived compound, a method for manufacturing the same, and an application thereof and, more particularly, to a camphor-derived compound used as a chiral catalyst, a method for manufacturing the same, and an application to catalyze asymmetric addition of an organic zinc to an aldehyde using the same.

2. Description of Related Art

When an enzyme performs catalysis in an organism, owing to its specific conformation in the structure, it can differentiate between two enantiomers having contrary chirality and catalyze only one in a specific configuration. Accordingly, a small difference in a chiral center of enantiomers can cause entirely different to even completely contrary physiological reactions or symptoms, and some examples are demonstrated as follows. Firstly, referring to glucoses in food, dextroglucose

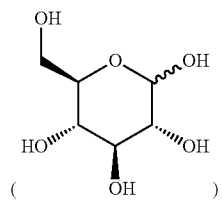 [SMILES: OC[C@H]1OC(O)[C@H](O)[C@@H](O)[C@@H]1O]

tastes sweet and can be ingested to afford energy in a human body. Although levoglucosan

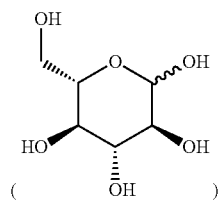 [SMILES: OC[C@@H]1OC(O)[C@@H](O)[C@H](O)[C@H]1O]

also tastes sweet, it can not be ingested and will be excreted outside the human body. Secondly, in regard to carvone used as flavor additives, S-form carvone

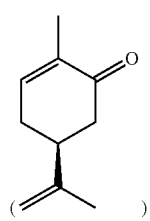

has a flavor of cilantro but R-form

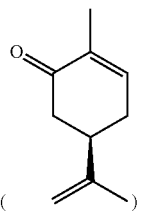

has a flavor of mint. Thirdly, with regard to a common amino acid asparagine, S-form asparagine

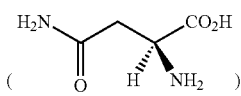

tastes bitter, but R-form asparagine

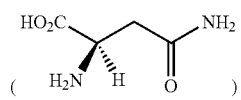

tastes sweet. Fourthly, with relation to a medicine Dopa, S-form dopa

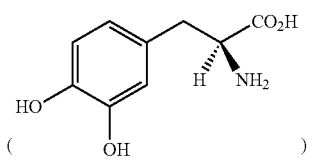 [SMILES: N[C@@H](Cc1ccc(O)c(O)c1)C(=O)O]

is widely used as a medicine for treatment of Parkinson's disease, but R-form dopa

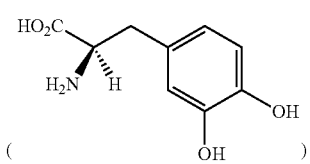 [SMILES: N[C@H](Cc1ccc(O)c(O)c1)C(=O)O]

is a poison causing osteoporosis. Fifthly, in relation to a medicine Naproxen, S-form naproxen

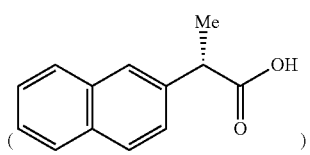 [SMILES: C[C@H](C(=O)O)c1ccc2ccccc2c1]

is an anti-inflammative anodyne having sustaining efficacy, but R-form naproxen

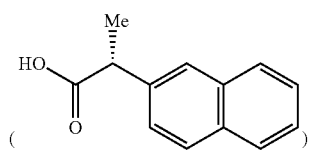 [SMILES: C[C@@H](C(=O)O)c1ccc2ccccc2c1]

can cause serious damage to kidneys.

However, in common syntheses, S-form and R-form enantiomers are simultaneously produced. If the enantiomers need to be used in an organism, syntheses or purification are required to isolate one enantiomer having high optical activity and single configuration.

Among methods for obtaining a pure compound with specific chirality, asymmetric synthesis is the most applicative and potential method. In this method, a chiral compound is used to provide a source of chirality so that the reactant forms an asymmetric plane to induce asymmetric reaction. Such method can be classified into three types: (A) chiral reagent: a reactant is asymmetrically reacted with a chiral reagent formed of chiral molecules; (B) chiral auxiliary: a reactant is combined to a chiral molecule to form an asymmetric plane so as to react with other reagents and the chiral auxiliary can be retrieved after the reaction; and (C) chiral catalyst: a chiral molecule and a reactant or reagent form an intermediate having high reactivity for asymmetric reaction, and a large amount of a product having optical activity can be obtained in the presence of a small amount of the chiral catalyst.

Since secondary alcohols having optical activity exist commonly in the structure of many natural products and drugs (for example, Orphenadrine, Neobenodine, Carbinoxamine, Efavirenz, Fostriencin, and Camptothecin), how to synthesize such secondary alcohols becomes an important topic. Currently, methods for constructing chiral centers in secondary alcohols can be classified into three types: (A) asymmetric reduction of ketones; (B) open-ring reaction of chiral epoxy compounds; and (C) asymmetric addition of metal nucleophilic reagents to aldehydes.

In the methods delineated above, metal zinc has low price, cytotoxicity, and effects to a human body, and thus is appropriate for catalysis. In asymmetric addition of organic zincs to aldehydes, catalysis performed by proper chiral catalysts is potential to give secondary alcohols having high optical activity.

SUMMARY OF THE INVENTION

The object of the present invention is to provide a camphor-derived compound as represented in the following formula (I):

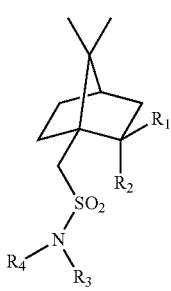

Formula (I)

In the formula (I), $R_1$ and $R_2$ independently are $-OR_a$, $-SR_b$, cyano, $-CH_2NH_2$, or

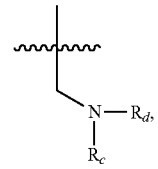

and when $R_1$ is $-OR_a$ or $SR$, $R_2$ is cyano, $-CH_2NH_2$, or

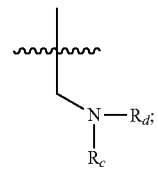

when $R_1$ is cyano, $-CH_2NH_2$, or

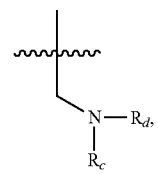

$R_2$ is $-OR_a$ or $SR_b$, wherein $R_a$ is H or silyl substituted by one to three $C_{1-10}$ alkyl, $R_b$ is H or $C_{1-10}$ alkyl substituted by $C_{6-14}$ aryl, $R_c$ and $R_d$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_c$ and $R_d$ are conjugated to form $-(CH_2)_m Z(CH_2)_n-$, wherein m and n are 1, 2, or 3, Z is $-CH_2-$, $-NH-$, $-O-$, or $-S-$; or $R_1$ and $R_2$ are combined to form $=O$, or $=S$; and $R_3$ and $R_4$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_3$ and $R_4$ are conjugated to form $-(CH_2)_m Z(CH_2)_n-$, wherein m and n are 1, 2, or 3, Z is $-CH_2-$, $-NH-$, $-O-$, or $-S-$.

In one aspect of the camphor-derived compound, $R_1$ is thiol or hydroxyl; $R_2$ is

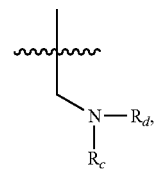

wherein $R_c$ and $R_d$ are conjugated to form $-(CH_2)_m Z (CH_2)_n-$; Z is $-O-$ and a sum of m and n is 3 or 4; and $R_3$ and $R_4$ independently are $C_{1-10}$ alkyl.

In another aspect of the camphor-derived compound, $R_1$ and $R_2$ are combined to form $=O$ or $=S$.

In further another aspect of the camphor-derived compound, $R_2$ is thiol or hydroxyl; $R_1$ is

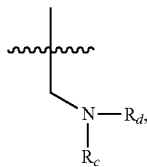

wherein $R_c$ and $R_d$ are conjugated to form —$(CH_2)_m Z(CH_2)_n$—; Z is —O— and a sum of m and n is 3 or 4; $R_3$ and $R_4$ independently are $C_{1-10}$ alkyl.

Another object of the present invention is to provide a method for manufacturing a camphor-derived compound, comprising the following steps:

(a) providing a compound represented by the following formula (Ia), formula (Ia)

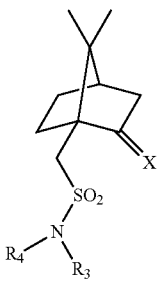

wherein X is O, or S, $R_3$ and $R_4$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_3$ and $R_4$ are conjugated to form —$(CH_2)_m Z(CH_2)_n$—, wherein m and n are 1, 2, or 3, Z is —$CH_2$—, —NH—, —O—, or —S—; and (b) forming a compound represented by the following formula (I) from the compound represented by the formula (Ia), formula (I)

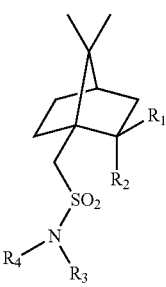

wherein $R_1$ and $R_2$ independently are —$OR_a$, —$SR_b$, cyano, —$CH_2NH_2$, or

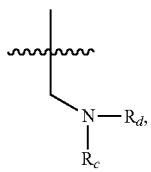

and when $R_1$ is —$OR_a$ or —$SR_b$, $R_2$ is cyano, —$CH_2NH_2$, or

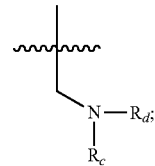

when $R_1$ is cyano, —$CH_2NH_2$, or

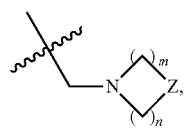

$R_2$ is —$OR_a$ or —$SR_b$, wherein $R_a$ is H or silyl substituted by one to three $C_{1-10}$ alkyl, $R_b$ is H or $C_{1-10}$ alkyl substituted by $C_{6-14}$ aryl, $R_c$ and $R_d$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_c$ and $R_d$ are conjugated to form —$(CH_2)_m Z(CH_2)_n$—, wherein m and n are 1, 2, or 3, Z is —$CH_2$—, —NH—, —O—, or —S—.

In one aspect of the method, in the step (a) the compound of the formula (Ia) in which X is S, is formed by reacting the compound of the formula (Ia) in which S is O with a Lawesson's reagent. In the step (b) the compound of the formula (I) in which $R_1$ and $R_2$ independently are benzylthiol and cyano, is formed by reacting benzyl halide with the compound of formula (I) in which $R_1$ and $R_2$ independently are thiol and cyano formed after the compound of the formula (Ia) in which X is S, is reacted with silyl cyanide. The compound of the formula (I) in which $R_1$ and $R_2$ independently are benzylthiol and cyano, is reduced to form the compound of the formula (I) in which $R_1$ is benzylthiol and $R_2$ is —$CH_2NH_2$, followed by N-alkylation with $W_1$—$(CH_2)_m Z(CH_2)_n$—$W_2$ to form the compound of the formula (I) in which $R_2$ is

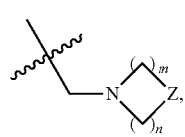

wherein $W_1$ and $W_2$ are leaving groups. The compound of the formula (I) in which $R_2$ is benzylthiol, is reduced to form the compound of the formula (I) in which $R_1$ is thiol.

In another aspect of the method, in the step (b) the compound of formula (I) in which $R_1$ and $R_2$ independently are silyloxy and cyano formed after the compound of the formula (Ia) in which X is O, is reacted with silyl cyanide, is reduced to form the compound of the formula (I) in which $R_1$ and $R_2$ independently are hydroxyl and —$CH_2NH_2$, followed by N-alkylation with $W_1$—$(CH_2)_mZ(CH_2)_n$—$W_2$ to form the compound of the formula (I) in which $R_2$ is

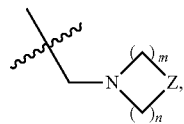

wherein $W_1$ and $W_2$ are leaving groups.

The abovementioned leaving groups can be diazonium salt, halogen, sulfonate, nitrate, phosphate, tetraalkylammonium salt, ester, and so on. For example, —$N_2^+$, —$OR'_2{}^+$, —$OSO_2C_4F_9$, —$OSO_2CF_3$, —$OSO_2F$, —OTs, —OMs, —I, —Br, —$OH_2{}^+$, —Cl, —$OHR'^+$, —$ONO_2$, —$OPO(OH)_2$, —$SR'_2{}^+$, —$NR'_3{}^+$, —F, —OCOR', and so forth. R' can be alkyl and aryl etc.

In further another aspect of the method, in the step (b), the compound of the formula (I) in which $R_1$ and $R_2$ independently are hydroxyl and

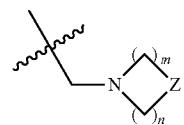

is formed by reacting the compound of the formula (Ia) in which X is S with

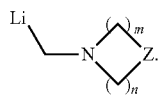

Another object of the present invention is to provide a method for asymmetric addition of an organic zinc to an aldehyde, comprising the following step: reacting $R_5C(O)H$ and $R_6ZnR_7$ in presence of a catalyst represented by the following formula (I), Formula (I)

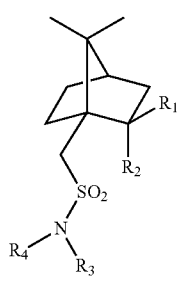

wherein $R_1$ and $R_2$ independently are hydroxyl, thiol, or

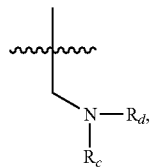

and when $R_1$ is hydroxyl or thiol, $R_2$ is

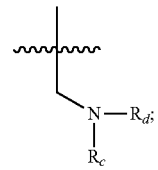

when $R_1$ is

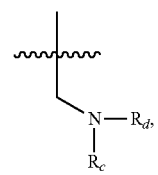

$R_2$ is hydroxyl or thiol, wherein $R_c$ and $R_d$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_c$ and $R_d$ are conjugated to form —$(CH_2)_mZ(CH_2)_n$—, wherein m and n are 1, 2, or 3, Z is —$CH_2$—, —NH—, —O—, or —S—;

$R_3$ and $R_4$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_3$ and $R_4$ are conjugated to form —$(CH_2)_mZ(CH_2)_n$—, wherein m and n are 1, 2, or 3, Z is —$CH_2$—, —NH—, —O—, or —S—; and $R_5$, $R_6$ and $R_7$ independently are $C_{1-10}$ alkyl, $C_{2-10}$ alkenyl, $C_{5-14}$ cycloalkyl, $C_{4-13}$ heterocycloalkyl, $C_{5-14}$ cycloalkenyl, $C_{5-14}$ heterocycloalkenyl, $C_{6-14}$ aryl, or $C_{4-13}$ heteroaryl, wherein the heterocycloalkyl, the heterocycloalkenyl and the heteroaryl have at least one heteroatom selected from the group consisting of O, S, Se, and N, wherein the $C_{1-10}$ alkyl, the $C_{2-10}$ alkenyl, the $C_{5-14}$ cycloalkyl, the $C_{4-13}$ heterocycloalkyl, the $C_{5-14}$ cycloalkenyl, the $C_{1-14}$ heterocycloalkenyl, the $C_{6-14}$ aryl, or the $C_{4-13}$ heteroaryl is optionally substituted by $C_{1-10}$ alkyl, halogen, cyano, —$CO_2$—$C_{1-10}$ alkyl, —$CO_2$—$C_{2-10}$ alkenyl, $C_{1-10}$ haloalkyl, $C_{2-10}$ alkenyl, $C_{1-10}$ alkoxyl, $C_{5-14}$ cycloalkyl, $C_{4-13}$ heterocycloalkyl, $C_{5-14}$ cycloalkenyl, $C_{1-14}$ heterocycloalkenyl, $C_{6-14}$ aryl, or $C_{4-13}$ heteroaryl.

In one aspect of the method for asymmetric addition of an organic zinc to an aldehyde, the catalyst of the formula (I) is used in an amount of 0.1-10 mol % based on a mole amount of the aldehyde $R_5C(O)H$.

In one aspect of the method for asymmetric addition of an organic zinc to an aldehyde, the organic zinc $R_6ZnR_7$ is used in an amount of 0.5-5 equivalents based on the amount of the aldehyde $R_5C(O)H$.

In detail, the compound of the formula (I) is an assistant to enantioselectively asymmetric addition of an organic zinc (i.e. $R_6ZnR_7$) to an aldehyde (i.e. $R_5C(O)H$). That is, the compound of the formula (I) can increase the enantioselectivity of the asymmetric addition. Based on the specific spacial configuration of the compound of the formula (I) and the conformation, the spacial barrier, etc. of the functional groups of the aldehyde, one of the compounds of the formula (II-1) and (II-2) can be major in the asymmetric addition. Alternatively, one of the compounds of the formula (II-3) and (II-4) can be major in the asymmetric addition.

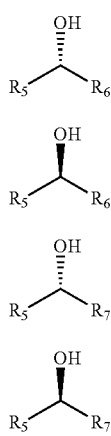

Preferably, $R_3$ and $R_4$ mentioned above independently are $C_{1-6}$ alkyl, $C_{5-10}$ cycloalkyl, $C_{4-10}$ heterocycloalkyl, $C_{6-10}$ aryl, or $C_{4-10}$ heteroaryl, wherein the heterocyclo and the heteroaryl have at least one heteroatom selected from the group consisting of O, S, Se, and N, or $R_3$ and $R_4$ are conjugated to form —$(CH_2)_m Z(CH_2)_n$—, wherein m and n are 1, 2, or 3, Z is —$CH_2$—, —NH—, —O—, or —S—. More preferably, $R_3$ and $R_4$ are functional groups which are spacial barriers.

Preferably, $R_5$, $R_6$, and $R_7$ said above independently are $C_{1-6}$ alkyl, $C_{2-10}$ alkenyl, $C_{5-10}$ cycloalkyl, $C_{4-10}$ heterocycloalkyl, $C_{5-10}$ cycloalkenyl, $C_{5-10}$ heterocycloalkenyl, $C_{6-10}$ aryl, or $C_{4-10}$ heteroaryl, wherein the heterocycloalkyl, the heterocycloalkenyl and the heteroaryl have at least one heteroatom selected from the group consisting of O, S, Se, and N, wherein the $C_{1-6}$ alkyl, the $C_{2-10}$ alkenyl, the $C_{5-10}$ cycloalkyl, the $C_{4-10}$ heterocycloalkyl, the $C_{5-10}$ cycloalkenyl, the $C_{5-10}$ heterocycloalkenyl, the $C_{6-10}$ aryl, or the $C_{4-10}$ heteroaryl are selectively substituted by $C_{1-6}$ alkyl, halogen, cyano, —$CO_2$—$C_{1-6}$ alkyl, —$CO_2$—$C_{2-10}$ alkenyl, $C_{1-6}$ haloalkyl, $C_{2-10}$ alkenyl, $C_{1-6}$ alkoxyl, $C_{5-10}$ cycloalkyl, $C_{4-10}$ heterocycloalkyl, $C_{5-10}$ cycloalkenyl, $C_{5-10}$ heterocycloalkenyl, $C_{6-10}$ aryl, or $C_{4-10}$ heteroaryl.

In the present invention, the term "alkyl" means a straight or branched hydrocarbon chain. Examples thereof include methyl, ethyl, n-propyl, isopropyl, n-butyl, isobutyl, t-butyl, n-pentyl, isopentyl, neopentyl, n-hexyl, 2-methylpentyl, 3-methylpentyl, 2,3-dimethylbutyl, and neohexyl, but are not limited thereto.

In the present invention, the term "alkenyl" means a straight or branched hydrocarbon chain containing one or more double bonds. Examples thereof include ethenyl, propenyl, 2-methylpropenyl, 1-methylpropenyl, allyl, and 1,4-butadienyl, but are not limited thereto.

In the present invention, the term "cycloalkyl" means a saturated cyclohydrocarbon having no heteroatom. Examples thereof include cyclopentyl, cyclohexyl, cycloheptyl, cyclooctyl, cyclononyl, and cyclodecanyl, but are not limited thereto.

In the present invention, the term "cycloalkenyl" means a non-aromatic cyclohydrocarbon containing one or more double bonds. Examples thereof include cyclopentenyl, cyclohexenyl, cycloheptenyl, cyclooctenyl, cyclononenyl, and cyclodecenyl, but are not limited thereto.

In the present invention, the term "heterocycloalkyl" means a saturated cyclohydrocarbon containing one or more heteroatoms such as N, O, S, and Se. Examples thereof include pyrrolidinyl, tetrahydrofuranyl, tetrahydrothiophenyl, piperidinyl, tetrahydropyranyl, thianyl, azepanyl, oxepanyl, thiepanyl, imidazolidenyl, pyrazolidinyl, oxazolidinyl, isoxazolidinyl, thiazolidinyl, isothiazolidinyl, dioxolanyl, oxathiolanyl, dithiolanyl, piperazinyl, morpholinyl, dithianyl, dioxanyl, trioxanyl, azocanyl, oxecanyl, and thiocanyl, but are not limited thereto.

In the present invention, the term "heterocycloalkenyl" means a non-aromatic cyclohydrocarbon containing one or more heteroatoms such as N, O, S, and Se and one or more double bonds. Examples thereof include pyranyl, thiopyranyl, imidazolinyl, pyrazolinyl, oxazolinyl, isoxazolinyl, thiazolinyl, and isothiazolinyl, but are not limited thereto.

In the present invention, the term "aryl" means an aromatic group which is a 6-carbon monocyclic, 10-carbon bicyclic, or 14-carbon tricyclic aromatic group having no heteroatoms. Examples thereof include phenyl, naphthyl, anthracenyl, benzocyclobutene, and phenanthrenyl, but are not limited thereto.

In the present invention, the term "heteroaryl" means an aromatic group which has one or more heteroatoms such as N, O, S, and Se and is 5-8 membered monocyclic, 8-12 membered bicyclic, or 11-14 membered tricyclic. Examples thereof include furanyl, benzofuranyl, isobenzofuranyl, pyrrolyl, indolyl, isoindolyl, thiophenyl or thienyl, benzothiophenyl, benzo[c]thiophenyl, imidazolyl, benzimidazolyl, purinyl, pyrazolyl, indazolyl, oxazolyl, benzoxazolyl, isoxazolyl, benzisoxazolyl, thiazolyl, benzothiazolyl, pyridyl, quinolinyl, isoquinolinyl, pyrazinyl, quinoxalinyl, acridinyl, pyrimidinyl, quinazolinyl, pyridazinyl, cinnolinyl, dithiazolyl, oxadiazolyl, thiadiazolyl, tetrazolyl, oxazinyl, thiazinyl, triazinyl, and tetrazinyl, but are not limited thereto.

The alkyl, alkenyl, cycloalkyl, heterocycloalkyl, cycloalkenyl, heterocycloalkenyl, aryl and heteroaryl depicted above include substituted and unsubstituted groups if no particular indication is provided. The term "substituted" means that one or more hydrogens are replaced with same or different substituents. The substituents include, for example, halo such as F, Cl, Br, and I, hydroxyl, amino, alkylamino, arylamino, dialkylamino, diarylamino, cyano, nitro, thoil or mercapto, carbonyl, carbamido, carbamyl, carboxyl, thiocyanato, sulfonamido, alkyl, alkenyl, alkoxyl, haloalkyl i.e. alkyl substituted by one or more halogens, cycloalkenyl, heterocycloalkenyl, aryl, heteroaryl, cycloalkyl, heterocycloalkyl, $CO_2$-alkyl and $CO_2$-alkenyl.

Other objects, advantages, and novel features of the invention will become more apparent from the following detailed description when taken in conjunction with the accompanying drawings.

BRIEF DESCRIPTION OF THE DRAWINGS

None.

DETAILED DESCRIPTION OF THE PREFERRED EMBODIMENT

Example 1

Synthesis of β-Aminoalcohol

With reference to the following scheme 1, it demonstrates the preparation of β-aminoalcohol 34.

Scheme 1

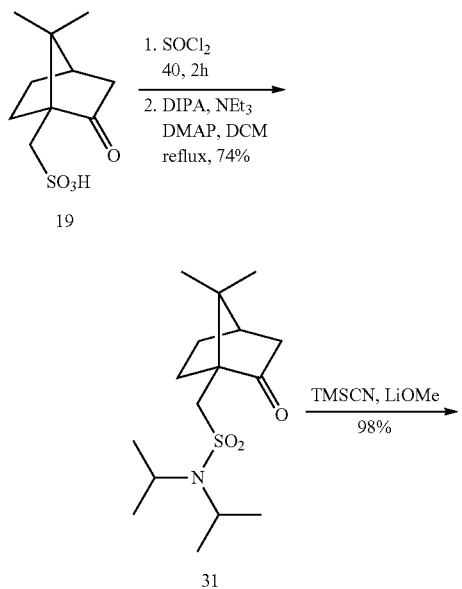

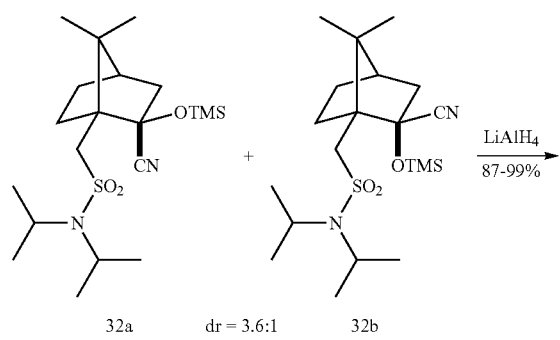

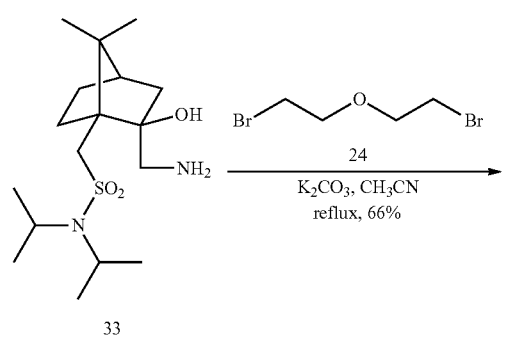

(i) Synthesis of Compound 1

Scheme 1a

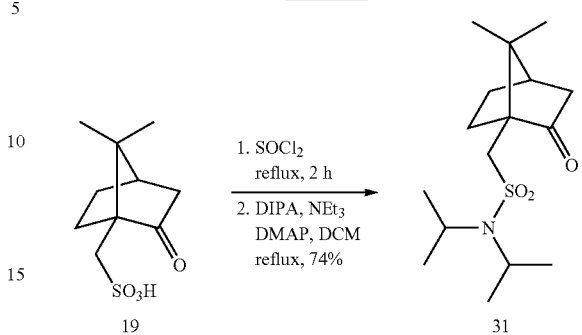

With reference to Scheme 1a illustrated above, compound 19 (10.02 g, 43.1 mmol) and SOCl$_2$ (10 ml, 137 mmol) were added in a 50-ml round-bottomed flask, refluxed for 2 hours, cooled to room temperature, and then poured into iced hexane (100 ml) for recrystalization. The resultant mixture was filtrated to give a bright white sheet solid. The solid was dissolved in dichloromethane (10 ml) and slowly dropwise added to a mixture containing 4-N,N-dimethylaminopyridine (0.53 g, 4.3 mmol), dichloromethane (20 ml), diisopropylamine (9.1 ml, 64.7 mmol), and triethylamine (4.4 ml, 43.1 mmol) in a 100-ml round-bottomed flask. The resultant mixture was refluxed at 50° C. for 2 hours, neutralized to be neutral by 3 N HCl aqueous solution, and then extracted with dichloromethane (20 ml×3). The resultant organic phase was dried with anhydrous sodium sulfate, filtrated, and then condensed. The crude extract was purified by chromatography (eluent:ethyl acetate:n-hexane=1:8) to give a white solid 31 (11.1 g, 74%), i.e. 7,7-Dimethyl-2-oxo-bicyclo[2.2.1]hept-1-yl-N,N-diisopropyl-methanesulfonamide). The data of the compound are listed as follows:

$^1$H-NMR (400 MHz, CDCl$_3$): δ 3.72 (septet, J=6.8 Hz, 2H), 3.26 (d, J=14.4 Hz, 1H), 2.72 (d, J=14.4 Hz, 1H), 2.56-2.49 (m, 1H), 2.30 (dt, J=4.0, 18.4 Hz, 1H), 2.02-1.92 (m, 2H), 1.85 (d, J=18.4 Hz, 1H), 1.58-1.51 (m, 1H), 1.34-1.25 (m, 13H), 1.10 (s, 3H), 0.82 (s, 3H).

$^{13}$C-NMR (100 MHz, CDCl$_3$): δ 215.4 (C), 58.7 (C), 51.1 (CH$_2$), 48.2 (CH), 47.4 (C), 42.8 (CH), 42.5 (CH$_2$), 26.7 (CH$_2$), 25.1 (CH$_2$), 22.4 (CH$_3$), 22.0 (CH$_3$), 20.1 (CH$_3$), 19.7 (CH$_3$).

(ii) Synthesis of Compounds 32a and 32b

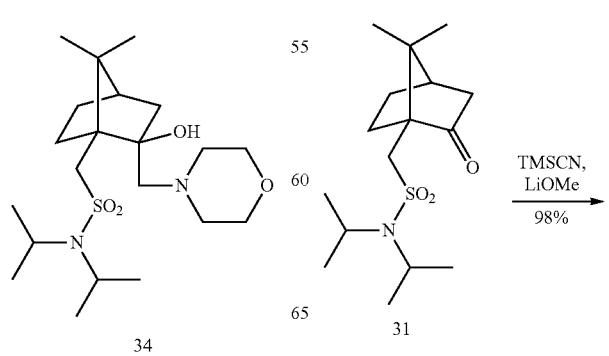

13

-continued

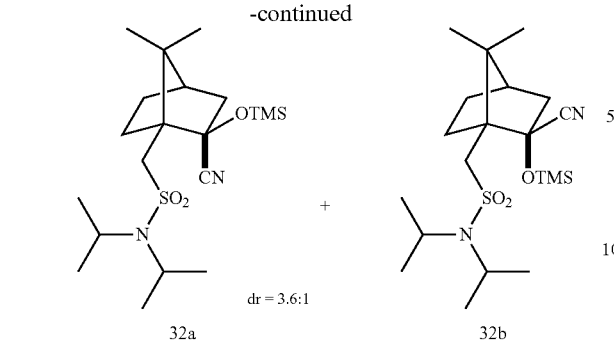

32a  dr = 3.6:1

32b  dr = 3.6:1

With reference to Scheme 1b mentioned above, lithium methoxide (4 mg, 0.1 mmol), anhydrous tetrahydrofuran (10 ml), and trimethylsilyl cyanide (0.3 ml, 2.3 mmol) were added in sequence in a 25-ml dry round-bottomed flask and stirred at room temperature for 10 minutes. Compound 31 (0.5 g, 1.6 mmol) was added in the flask and stirred at room temperature for 12 hours, followed by addition of a 10% sodium carbonate aqueous solution to cease reaction. The resultant mixture was extracted by dichoromethane (20 ml×3). The organic phase was dried with anhydrous sodium sulfate, filtrated, and condensed. The resultant crude extract was purified by chromatography (eluent:ethyl acetate:n-hexane=1:10) to give white solids 32a (11.1 g, 74%) and 32b (0.1 g, 21%).

Compound 32a is (2R)-2-Cyano-7,7-dimethyl-2-trimethyl-silanyloxy-bi-cyclo[2.2.1]hept-1-yl-N,N-diisopropyl-methanesulfonamide and its data are listed as follows:

$^1$H-NMR (400 MHz, CDCl$_3$): δ 3.74 (septet, J=6.8 Hz, 2H), 3.32 (d, J=13.8 Hz, 1H), 2.64 (d, J=13.8 Hz, 1H), 2.29-2.24 (m, 1H), 2.20-2.08 (m, 3H), 1.85-1.78 (m, 2H), 1.60-1.58 (m, 1H), 1.32-1.26 (m, 12H), 0.96 (s, 3H), 0.94 (s, 3H), 0.26 (s, 9H).

$^{13}$C-NMR (100 MHz, CDCl$_3$): δ 121.5 (C), 54.7 (C), 51.5 (CH$_2$), 50.3 (CH$_2$), 50.0 (C), 48.2 (CH), 44.3 (CH), 27.6 (CH$_2$), 26.4 (CH$_2$), 22.3 (CH$_3$), 22.2 (C), 21.5 (CH$_3$), 20.1 (CH$_3$), 1.1 (CH$_3$).

IR: cm$^{-1}$ (neat) 2959, 2879, 2232, 1456, 1392, 1367, 1337, 1253.

HRMS: Calc. for C$_{20}$H$_{38}$N$_2$O$_3$SSi: 414.2372. (EI) 414.2378.

Specific rotation: $[α]_D^{30.4}$ –3.31 (c 1.0, CH$_2$Cl$_2$).

M.p.: 98.0-98.8° C.

Compound 32b is (2S)-2-Cyano-7,7-dimethyl-2-trimethylsilanyloxy-bicyclo[2.2.1]hept-1-yl-N,N-diisopropyl-methanesulfonamide and its data are listed as follows:

$^1$H-NMR (400 MHz, CDCl$_3$): δ 3.71 (septet, J=6.8 Hz, 2H), 3.22 (d, J=14.0 Hz, 1H), 2.93 (d, J=14.0 Hz, 1H), 2.57 (dt, J=4.0, 14.0 Hz, 1H), 2.42-2.36 (m, 1H), 1.95-1.89 (m, 1H), 1.79-1.74 (m, 2H), 1.48 (d, J=13.2 Hz, 1H), 1.29-1.18 (m, 13H), 1.08 (s, 3H), 0.99 (s, 3H), 0.21 (s, 9H).

$^{13}$C-NMR (100 MHz, CDCl$_3$): δ 122.4 (C), 76.4 (C), 57.2 (C), 54.5 (CH2), 50.2 (C), 48.2 (CH), 46.2 (CH$_2$), 44.6 (CH), 26.7 (CH$_2$), 23.9 (CH$_2$), 22.2 (CH$_3$), 22.2 (CH$_3$), 21.7 (CH$_3$), 20.1 (CH$_3$), 1.0 (CH$_3$).

14

(iii) Synthesis of Compound 33

Scheme 1c

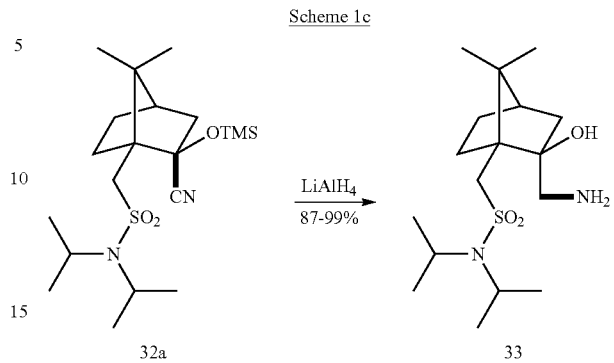

32a  →  33

With reference to Scheme 1c delineated above, lithium aluminum tetrahydride (1.4 g, 36.9 mmol) and anhydrous ether (200 ml) were added in a 500-ml dry round-bottomed flask. Compound 32a (5.0 g, 12.1 mmol) dissolved in anhydrous ether (75 ml) was slowly injected by a dry syringe into the flask at room temperature and stirred for 10 hours at room temperature. Deionized water (3.5 ml), 3 N NaOH aqueous solution (3.5 ml), and deionized water (14 ml) were added in sequence to stop reaction. The resultant mixture was washed with ethyl acetate and filtrated to remove aluminum salt. The organic phase collected was condensed to form a white solid 33 (4.1 g, 99%), i.e. (2R)-2-Aminomethyl-2-hydroxyl-7,7-dimethyl-bicyclo[2.2.1]hept-1-yl-N,N-diisopropyl-methane-sulfonamide), and its data was listed as follows:

$^1$H-NMR (400 MHz, CDCl$_3$): δ 3.72 (septet, J=6.8 Hz, 2H), 3.46 (d, J=14.4 Hz, 1H), 3.27 (d, J=12.6, 1H), 2.63 (d, J=14.4 Hz, 1H), 2.62 (d, J=12.6 Hz, 1H), 2.04-1.96 (m, 2H), 1.78-1.68 (m, 4H), 1.44 (br, 2H), 1.34 (s, 1H), 1.30 (d, J=6.8 Hz, 12H), 1.10-1.02 (m, 4H), 0.88 (s, 3H).

$^{13}$C-NMR (100 MHz, CDCl$_3$): δ 78.0 (C), 52.9 (CH$_2$), 52.6 (C), 51.6 (C), 48.7 (CH$_2$), 48.1 (CH), 45.3 (CH$_2$), 43.6 (CH), 27.0 (CH$_2$), 25.4 (CH$_2$), 22.4 (CH$_3$), 22.0 (CH$_3$), 20.9 (CH$_3$), 20.4 (CH$_3$).

IR: cm$^{-1}$ (neat) 3480, 3395, 3326, 2971, 2936, 2877, 1599, 1457, 1401, 1370, 1325.

HRMS: Calc. for C$_{17}$H$_{34}$N$_2$O$_3$S: 347.2290 (M+1$^+$). (FAB) 347.2371 (M+1$^+$).

Specific rotation: $[α]_D^{29.8}$ –8.01 (c 1.0, CH$_2$Cl$_2$).

M.p.: 128.2-129.4° C.

(iv) Synthesis of Compound 34

Scheme 1d

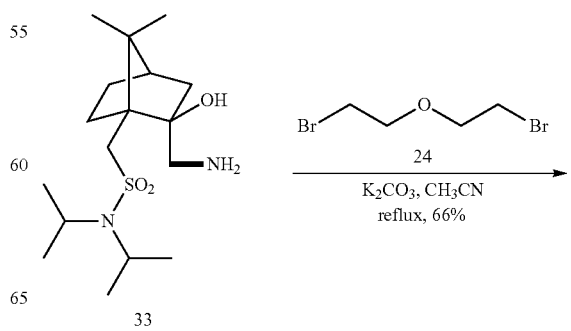

33

$\xrightarrow[\text{reflux, 66\%}]{\text{K}_2\text{CO}_3, \text{CH}_3\text{CN}}$

24

-continued

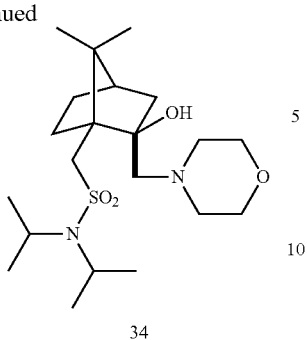

34

With reference to Scheme 1 d, Compound 33 (2.0 g, 5.8 mmol), $K_2CO_3$ (1.7 g, 11.5 mmol), and acetonitrile (50 ml) were added in a 100-ml round-bottomed flask, and 2-bromoethylether 24 (1.1 ml, 8.7 mmol) was also added. The resultant mixture was refluxed for 20 hours and cooled to room temperature, and water (30 ml) was added therein to dissolve solids. The mixture was condensed by reduced pressure to remove acetonitrile and extracted with dichloromethane (30 ml×3). The organic phase was washed with a saturated NaCl aqueous solution, dried with anhydrous sodium sulfate, filtrated, and condensed. The obtained crude extract was purified by chromatography (eluent:methanol:dichloromethane=1:40) to give a white solid 34 (1.6 g, 66%), i.e. (2R)-2-Hydroxyl-7,7-dimethyl-2-morpholin-4-yl-methyl-bicyclo[2.2.1]hept-1-yl-N,N-diisopropyl-methanesulfonamide), and its data are depicted as follows:

$^1$H-NMR (400 MHz, $CDCl_3$): δ 5.38 (br, 1H), 3.77-3.64 (m, 6H), 3.52 (d, J=14.2 Hz, 1H), 3.41 (d, J=12.4 Hz, 1H), 2.71-2.66 (m, 2H), 2.58 (d, J=14.2 Hz, 1H), 2.47-2.44 (m, 2H), 2.22 (d, J=12.4 Hz, 1H), 2.06-2.01 (m, 1H), 1.97-1.89 (m, 1H), 1.75-1.65 (m, 3H), 1.46 (d, J=12.4 Hz, 1H), 1.29 (d, J=6.8 Hz, 12H), 1.14-1.04 (m, 4H), 0.85 (s, 3H).

$^{13}$C-NMR (100 MHz, $CDCl_3$): δ 74.4 (C), 67.0 ($CH_2$), 66.0 ($CH_2$), 54.5 (C), 53.6 ($CH_2$), 53.0 ($CH_2$), 51.0 (C), 50.6 ($CH_2$), 48.1 (CH), 44.7 (CH), 27.2 ($CH_2$), 24.2 ($CH_2$), 22.4 ($CH_3$), 22.2 ($CH_3$), 20.8 ($CH_3$), 20.3 ($CH_3$).

IR: $cm^{-1}$ (neat) 3272, 2954, 2876, 2852, 1456, 1329.
HRMS: Calc. for $C_{21}H_{40}N_2O_4S$: 416.2709. (EI) 416.2704.
Specific rotation: $[α]_D^{29.6}$ −13.60 (c 1.0, $CH_2Cl_2$).
M.p.: 111.5-112.5° C.

Example 2

Synthesis of β-Amino Alcohol

Referring to Scheme 2 delineated below, it shows an alternative scheme for preparation of β-amino alcohol 34.

Scheme 2

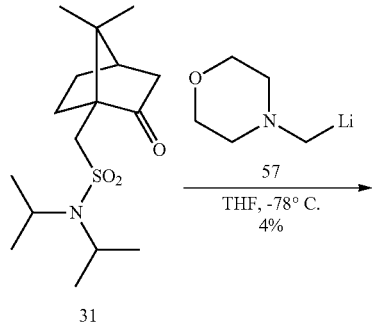

31

-continued

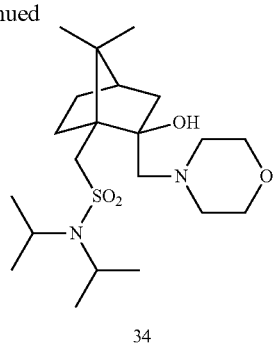

34

1-morpholinylmethyltributyl tin (0.3 g, 0.64 mmol) and anhydrous tetrahydrofuran (3 ml) were added in a 10-ml dry round-bottomed flask. The mixture was cooled to −78° C. and then n-butyl lithium (2.5 M, 0.24 ml) was added therein and stirred for 5 minutes. Compound 31 (0.1 g, 5 mmol) was dissolved in anhydrous tetrahydrofuran (1 ml) and added in the flask. The reaction was performed at −78° C. for one hour and a saturated $NH_4Cl$ aqueous solution was added to cease the reaction. The mixture was extracted with dichloromethane (30 ml×3) and the organic phase was washed with a saturated NaCl aqueous solution, dried with anhydrous sodium sulfate, filtrated, and condensed. The obtained crude extract was purified by chromatography (eluent:methanol: dichloromethane=1:40) to give a white solid 34 (0.008 g, 4%), i.e., (2R)-2-Hydroxyl-7,7-dimethyl-2-morpholin-4-yl-methyl-bicyclo[2.2.1]hept-1-yl-N,N-diisopropyl-methanesulfonamide).

Example 3

Synthesis of β-Aminothiol

Referring to Scheme 3, it demonstrates a flowchart for preparation of β-aminothiol 40.

Scheme 3

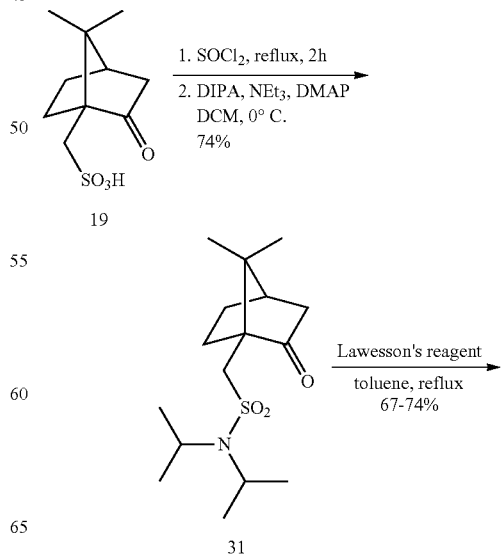

31

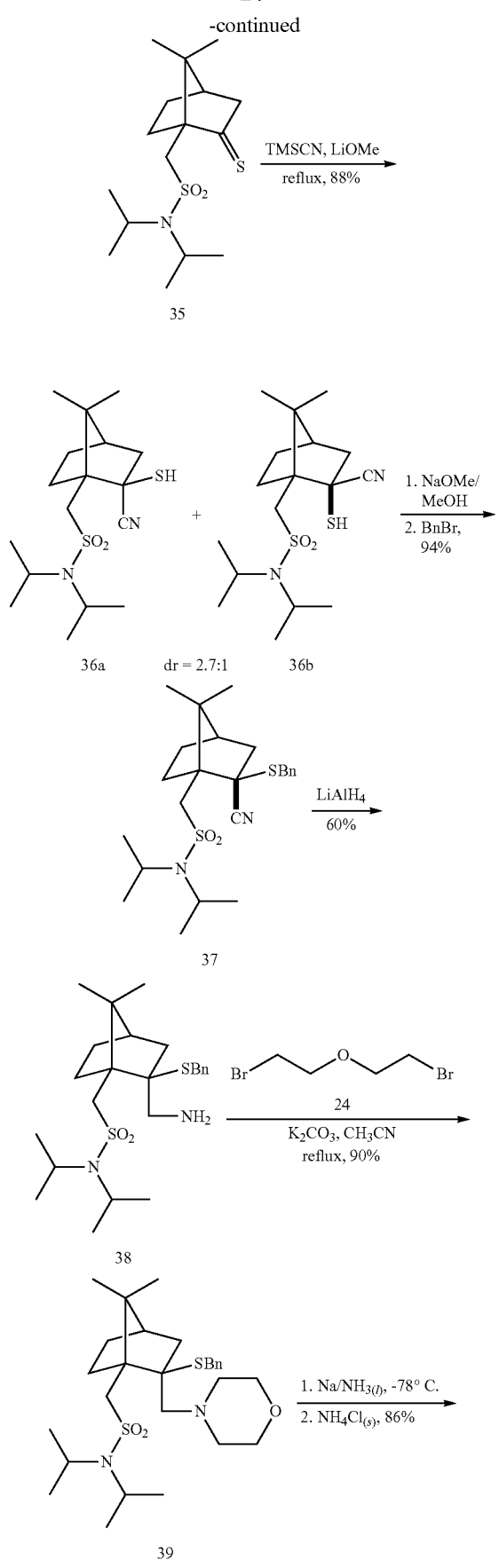

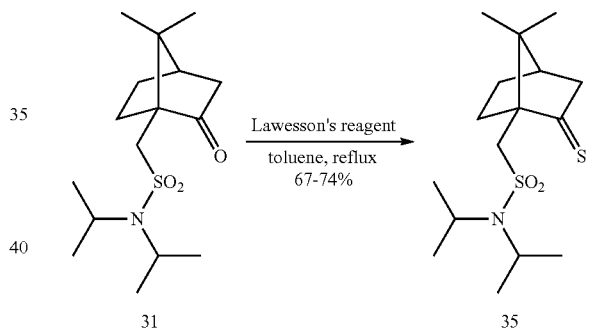

(i) Synthesis of Compound 31

It was prepared in the manner in accordance with the step (i) of Example 1.

(ii) Synthesis of Compound 35

With reference to Scheme 3a depicted above, Compound 31 (5.0 g, 15.9 mmol) and a Lawesson's reagent (3.9 g, 9.7 mmol) were added in a 50-ml round-bottomed flask and stood under vacuum for one hour, and then anhydrous methylbenzene (12 ml) was added. The mixture was refluxed for 6 hours, cooled to room temperature, filtrated, and then condensed. The obtained crude extract was purified by chromatography (eluent:ethyl acetate:n-hexane=1:10) to give an orange solid 35 (3.9 g, 74%), i.e., 7,7-dimethyl-2-thioxo-bicyclo[2.2.1]hept-1-yl-N,N-diisopropyl-methanesulfonamide), and its data are shown as follows:

$^1$H-NMR (400 MHz, CDCl$_3$): δ 3.87 (d, J=14.6 Hz, 1H), 3.77 (septet, J=6.8 Hz, 2H), 2.87 (d, J=14.6 Hz, 1H), 2.78-2.64 (m, 2H), 2.44 (d, J=20.8 Hz, 1H), 2.12-2.00 (m, 2H), 1.50-1.29 (m, 14H), 1.20 (s, 3H), 0.81 (s, 3H).

$^{13}$C-NMR (100 MHz, CDCl$_3$): δ 69.7 (C), 54.8 (CH$_2$), 53.9 (CH$_2$), 49.7 (C), 48.3 (CH), 44.9 (CH), 29.6 (CH$_2$), 27.0 (CH$_2$), 26.0 (C), 22.5 (CH$_3$), 22.0 (CH$_3$), 20.4 (CH$_3$), 19.7 (CH$_3$).

(iii) Synthesis of Compounds 36a and 36b

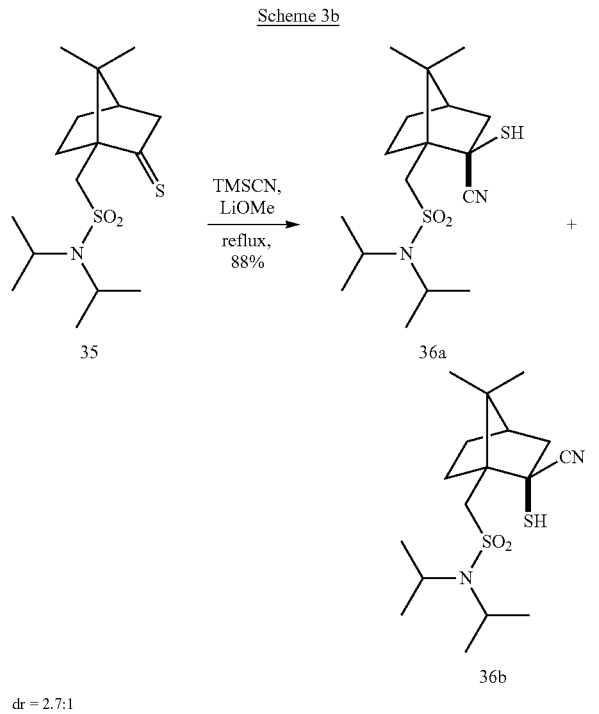

dr = 2.7:1

With reference to the aforesaid Scheme 3b, lithium methoxide (2.0 g, 44.6 mmol), anhydrous tetrahydrofuran (60 ml), and trimethylsilyl cyanide (4.5 ml, 35 mmol) were added in sequence in a 250-ml dry round-bottomed flask and stirred at room temperature for 10 minutes. Compound 35 (9.8 g, 29.7 mmol) was added in the flask and refluxed for 18 hours, followed by addition of a 10% sodium carbonate aqueous solution to cease reaction. The mixture was acidified with a 6 N HCl aqueous solution and extracted with dichoromethane (100 ml×3). The organic phase collected was dried with anhydrous sodium sulfate, filtrated, and condensed. The resultant crude extract was purified by chromatography (eluent:ethyl acetate:n-hexane:dichloromethane=1:5:0.5) to give white solids 36a (6.9 g, 64%) and 36b (2.6 g, 24%).

Compound 36a is (2R)-2-cyano-2-mercapto-7,7-dimethyl-bicyclo[2.2.1]hept-1-yl-N,N-diisopropyl-methane-sulfonamide) and its data are listed as follows:

$^1$H-NMR (400 MHz, CDCl$_3$): δ 3.95 (s, 1H), 3.77 (septet, J=6.8 Hz, 2H), 3.60 (d, J=13.8 Hz, 1H), 2.72 (d, J=13.8 Hz, 1H), 2.52-2.46 (m, 1H), 2.36 (d, J=13.6 Hz, 1H), 2.31-2.26 (m, 1H), 2.11-2.03 (m, 1H), 1.90-1.84 (m, 2H), 1.51-1.44 (m, 1H), 1.34-1.32 (m, 12H), 1.03 (s, 3H), 0.93 (s, 3H).

$^{13}$C-NMR (100 MHz, CDCl$_3$): δ 123.0 (C), 53.6 (C), 53.4 (CH$_2$), 51.5 (C), 48.5 (CH), 47.6 (CH$_2$), 44.4 (CH), 44.1 (C), 30.9 (CH$_2$), 26.4 (CH$_2$), 22.5 (CH$_3$), 22.1 (CH$_3$), 21.7 (CH$_3$), 20.4 (CH$_3$).

IR: cm$^{-1}$ (neat) 2972, 2881, 2228, 1602, 1495, 1456, 1395, 1371, 1336.

HRMS: Calc. for C$_{17}$H$_{30}$N$_2$O$_2$S$_2$: 358.1749. (EI) 358.1741.

Specific rotation: $[\alpha]_D^{29.6}$ −18.01 (c 1.0, CH$_2$Cl$_2$).

M.p.: 176.0-176.5° C.

Compound 36b is (2S)-2-cyano-2-mercapto-7,7-dimethyl-bicyclo[2.2.1]hept-1-yl-N,N-diisopropyl-methanesulfonamide and its data are listed as follows:

$^1$H-NMR (400 MHz, CDCl$_3$): δ 4.49 (s, 1H), 3.74 (septet, J=6.8 Hz, 2H), 3.34 (d, J=14.2 Hz, 1H), 2.80 (d, J=14.2 Hz, 1H), 2.79-2.70 (m, 2H), 1.93-1.87 (m, 1H), 1.81-1.76 (m, 2H), 1.44 (d, J=13.6 Hz, 1H), 1.31-1.20 (m, 13H), 1.10 (s, 3H), 0.98 (s, 3H).

$^{13}$C-NMR (100 MHz, CDCl$_3$): δ 123.4 (C), 55.9 (CH$_2$), 54.9 (C), 53.2 (C), 48.6 (CH), 46.3 (CH$_2$), 43.5 (CH), 42.9 (C), 27.8 (CH$_2$), 26.7 (CH$_2$), 22.2 (CH$_3$), 22.0 (CH$_3$), 20.0 (CH$_3$).

(iii) Synthesis of Compound 37

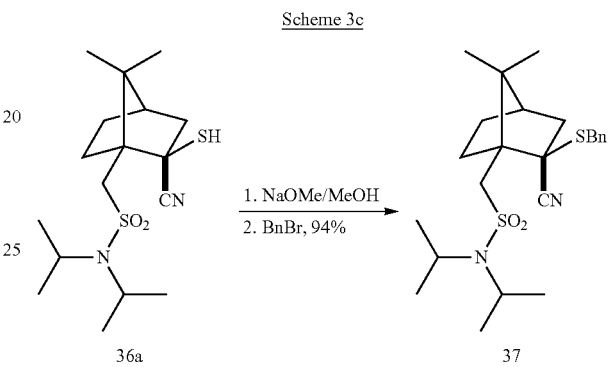

With reference with Scheme 3c delineated above, sodium methoxide (0.2 g, 3.4 mmol) and methanol (5 ml) were added in a 25-ml dry round-bottomed flask. Compound 36a (1.0 g, 2.7 mmol) dissolved in methanol (5 ml) was slowly added into the flask and stirred for 30 minutes at room temperature, and then Benzyl bromide (0.5 ml, 6.5 mmol) was further added. The mixture was stirred for 6 hours at room temperature and then condensed to remove the solvent. Water (20 ml) was added to dissolve solids. The mixture was extracted with ethyl acetate (20 ml×3) and the organic phase collected was washed with a saturated NaCl aqueous solution, dried with anhydrous sodium sulfate, filtrated, and then condensed. The resultant crude extract was purified by chromatography (eluent:ethyl acetate:n-hexane=1:6) to give a white solid 37 (1.1 g, 94%), i.e., (2R)-2-benzyl-sulfanyl-2-cyano-7,7-dimethyl-bicyclo[2.2.1]hept-1-yl-N,N-diisopropyl-methane-sulfonamide) and its data are depicted below:

$^1$H-NMR (400 MHz, CDCl$_3$): δ 7.38-7.22 (m, 5H), 4.25 (d, J=11.8 Hz, 1H), 4.16 (d, J=11.8 Hz, 1H), 3.78 (septet, J=6.4, 2H), 3.47 (d, J=14.0 Hz, 1H), 2.79 (d, J=14.0 Hz, 1H), 2.49-2.20 (m, 4H), 1.88-1.81 (m, 2H), 1.48-1.29 (m, 13H), 1.07 (s, 3H), 0.96 (s, 3H).

$^{13}$C-NMR (100 MHz, CDCl$_3$): δ 136.1 (C), 129.4 (CH), 128.5 (CH), 127.4 (CH), 120.1 (C), 54.7 (C), 53.2 (CH$_2$), 51.2 (C), 51.0 (C), 49.8 (CH$_2$), 48.3 (CH), 45.0 (CH), 38.3 (CH$_2$), 30.9 (CH$_2$), 26.3 (CH$_2$), 22.8 (CH$_3$), 21.9 (CH$_3$), 21.6 (CH$_3$), 21.2 (CH$_3$).

IR: cm$^{-1}$ (neat) 2971, 2880, 2228, 1602, 1495, 1456, 1395, 1371, 1336.

HRMS: Calc. for C$_{24}$H$_{36}$N$_2$O$_2$S$_2$: 448.2218. (EI) 448.2224.

Specific rotation: $[\alpha]_D^{29.5}$ +43.64 (c 1.0, CH$_2$Cl$_2$).

M.p.: 104.8-106.0° C.

(iv) Synthesis of Compound 38

Scheme 3d

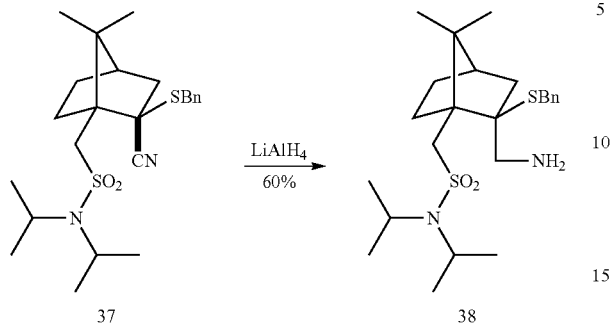

With reference to Scheme 1d delineated above, lithium aluminum tetrahydride (0.3 g, 6.6 mmol) and anhydrous ether (35 ml) were added in a 100-ml dry round-bottomed flask. Compound 37 (1.0 g, 2.2 mmol) dissolved in anhydrous ether (15 ml) was slowly injected by a dry syringe into the flask at room temperature and stirred for 10 hours at room temperature. Deionized water (0.5 ml), 3 N NaOH aqueous solution (0.5 ml), and deionized water (2 ml) were added in sequence to stop reaction. The resultant mixture was washed with ethyl acetate and filtrated to remove aluminum salt. The organic phase collected was purified by chromatography (eluent: methanol:dichloromethane=1:10) to give a light yellow oil 38 (0.6 g, 60%), i.e., (2R)-2-Aminomethyl-2-benzylsulfanyl-7, 7-dimethyl-bi-cyclo[2.2.1]hept-1-yl-N,N-diisopropyl-methanesulfonamide and its date are listed below:

$^1$H-NMR (400 MHz, CDCl$_3$): δ 7.35-7.21 (m, 5H), 3.74-3.63 (m, 4H), 3.53 (d, J=15.0 Hz, 1H), 3.03 (d, J=15.0 Hz, 1H), 2.83-2.77 (m, 2H), 2.47-2.35 (m, 2H), 2.22 (br, 2H), 1.91-1.81 (m, 2H), 1.77 (t, J=4.4 Hz, 1H), 1.33-1.12 (m, 17H), 1.02 (s, 3H).

$^{13}$C-NMR (100 MHz, CDCl$_3$): δ 137.4 (C), 129.1 (CH), 128.5 (CH), 127.0 (CH), 62.7 (C), 53.5 (CH$_2$), 52.9 (C), 52.7 (C), 49.4 (CH$_2$), 48.3 (CH), 44.3 (CH), 43.2 (CH$_2$), 33.3 (CH$_2$), 27.5 (CH$_2$), 27.1 (CH$_2$), 22.6 (CH$_3$), 22.4 (CH$_3$), 21.9 (CH$_3$), 21.5 (CH$_3$).

IR: cm$^{-1}$ (neat) 3375, 3306, 2952, 2873, 1602, 1495, 1454, 1390, 1369.

HRMS: Calc. for C$_{24}$H$_{40}$N$_2$O$_2$S$_2$: 453.2531 (M+1$^+$). (FAB) 453.2602 (M+1$^+$).

Specific rotation: [α]$_D^{29.5}$ −23.33 (c 1.0, CH$_2$Cl$_2$).

(v) Synthesis of Compound 39

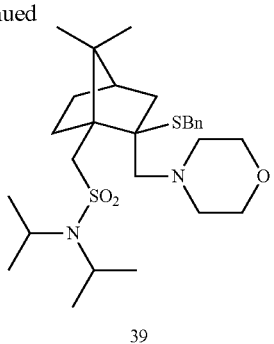

With reference to Scheme 3e, Compound 38 (1.2 g, 2.7 mmol), K$_2$CO$_3$ (0.8 g, 5.6 mmol), and acetonitrile (40 ml) were added in a 100-ml round-bottomed flask, and 2-bromoethylether 24 (0.5 ml, 4.1 mmol) was also added. The resultant mixture was refluxed for 24 hours and cooled to room temperature, and water (30 ml) was added therein to dissolve solids. The mixture was condensed by reduced pressure to remove acetonitrile and extracted with dichloromethane (30 ml×3). The organic phase was washed with a saturated NaCl aqueous solution, dried with anhydrous sodium sulfate, filtrated, and condensed. The obtained crude extract was purified by chromatography (eluent:ethyl acetate:n-hexane=1:6) to give a white solid 39 (1.3 g, 90%), i.e. (2R)-2-Benzylsulfanyl-7,7-dimethyl-2-morpholin-4-yl-methyl-bicyclo[2.2.1]hept-1-yl-N,N-diisopropyl-methane-sulfonamide and its data are depicted as follows:

$^1$H-NMR (400 MHz, CDCl$_3$): δ 7.36-7.20 (m, 5H), 4.01 (d, J=11.8 Hz, 1H), 3.95 (d, J=11.8 Hz, 1H), 3.83 (d, J=14.0 Hz, 1H), 3.74-3.66 (m, 6H), 3.09 (d, J=14.0 Hz, 1H), 2.91-2.86 (m, 3H), 2.67-2.63 (m, 3H), 2.26-2.19 (m, 2H), 1.94-1.88 (m, 1H), 1.84-1.71 (m, 2H), 1.46 (d, J=13.2 Hz, 1H), 1.31-1.28 (m, 12H), 1.24 (s, 3H), 1.21-1.14 (m, 1H), 1.02 (s, 3H).

$^{13}$C-NMR (100 MHz, CDCl$_3$): δ 137.9 (C), 129.1 (CH), 128.4 (CH), 126.8 (CH), 67.4 (CH$_2$), 66.5 (CH$_2$), 59.6 (C), 55.9 (CH$_2$), 55.3 (C), 54.6 (CH$_2$), 52.0 (C), 48.2 (CH), 45.4 (CH), 43.2 (CH$_2$), 34.7 (CH$_2$), 27.5 (CH$_2$), 26.8 (CH$_2$), 22.9 (CH$_3$), 22.4 (CH$_3$), 22.1 (CH$_3$), 21.7 (CH$_3$).

IR: cm$^{-1}$ (neat) 3061, 2951, 2871, 1602, 1495, 1453, 1390.

HRMS: Calc. for C$_{28}$H$_{46}$N$_2$O$_3$S$_2$: 522.2950. (EI) 552.2952.

Specific rotation: [α]$_D^{29.5}$ −39.50 (c 1.0, CH$_2$Cl$_2$).

M.p.: 96.2-97.2° C.

(iv) Synthesis of Compound 40

Scheme 3f

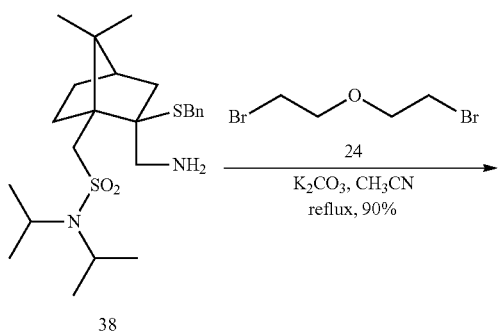

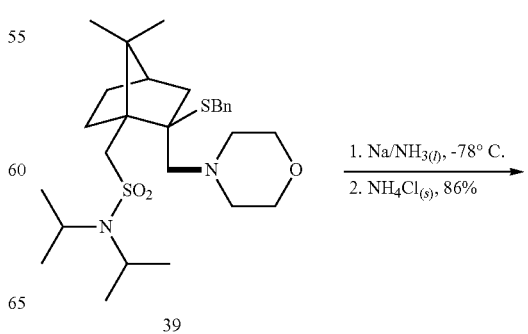

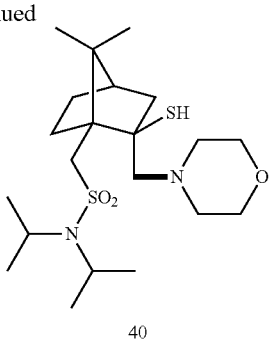

40

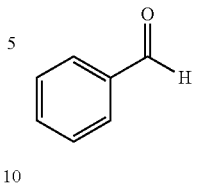

Scheme 4

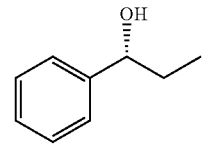

With reference to Scheme 3f, Compound 39 (1.1 g, 2.1 mmol) was dissolved in anhydrous tetrahydrofuran and $NH_3$ liquid containing sodium was added thereto at −78° C. The mixture was stirred for 4 hours at −78° C. and then $NH_4Cl$ solid was added to stop reaction. After $NH_3$ was evaporated, dichloromethane was added. The mixture was filtrated and then condensed by reduced pressure to afford a light yellow solid. The obtained crude extract was purified by chromatography (eluent:ethyl acetate:n-hexane=1:6) to give a white solid 40 (0.8 g, 86%), i.e., (2R)-2-aminomethyl-2-benzyl-sulfanyl-7,7-dimethyl-bi-cyclo[2.2.1]hept-1-yl-N,N-diisopropyl-methanesulfonamide) and its data are listed below:

$^1$H-NMR (400 MHz, $CDCl_3$): δ 5.30 (br, 1H), 3.98 (d, J=14.4 Hz, 1H), 3.76-3.65 (m, 6H), 3.19 (d, J=12.4 Hz, 1H), 2.75-2.67 (m, 2H), 2.69 (d, J=14.4 Hz, 1H), 2.46-2.37 (m, 2H), 2.29 (dt, J=3.2, 13.6 Hz, 1H), 2.20 (d, J=12.4 Hz, 1H), 2.11-1.95 (m, 2H), 1.80-1.68 (m, 3H), 1.31-1.13 (m, 13H), 1.06 (s, 3H), 0.91 (s, 3H).

$^{13}$C-NMR (100 MHz, $CDCl_3$): δ 67.2 ($CH_2$), 66.8 ($CH_2$), 55.7 (C), 55.6 (C), 55.2 ($CH_2$), 53.6 ($CH_2$), 52.0 ($CH_2$), 51.6 (C), 48.2 (CH), 45.6 (CH), 27.2 ($CH_2$), 25.9 ($CH_2$), 22.6 ($CH_3$), 22.1 ($CH_3$), 21.5 ($CH_3$), 20.8 ($CH_3$).

IR: $cm^{-1}$ (neat) 2967, 2877, 2851, 2385, 1458, 1400, 1370, 1330.

HRMS: Calc. for $C_{21}H_{40}N_2O_3S_2$: 432.2480. (EI) 432.2471.

Specific rotation: $[α]_D^{29.6}$−20.94 (c 1.0, $CH_2Cl_2$).

M.p.: 127.0-127.5° C.

Although the abovementioned examples only show the preparation of R-form compounds, S-form compounds can be prepared in the manner in accordance with the step 3c in which Compound 36a is substituted by Compound 36b or in accordance with the step 1c in which Compound 32a is substituted by Compound 32b.

Application Example 1

Asymmetric Addition of Diethyl Zinc to Aldehydes (i) Asymmetric Addition with Different Amounts of Chiral Ligand With reference to the following Scheme 4, it shows that ethyl in diethyl zinc is added to the aldehyde in the presence of β-amino thiol 40 used as a chiral ligand.

Compound 40 (the used amount thereof listed in Table 1) and benzaldehydes (2 mmol) placed in a 10-ml round-bottomed flask were stirred for 10 minutes at predetermined temperatures (shown in Table 1). Subsequently, diethyl zinc in n-hexane (1 M, 3 ml, 3 mmol) was added slowly along the inner wall of the flask. Posterior to several hours (shown in Table 1) of stirring, $NH_4Cl$ aqueous solution (1 N, 1 ml) was added to cease reaction, and then 1 N HCl aqueous solution was added for neutralization (pH=7). The organic and water phases were separated and the water phase was extracted with dichloromethane (20 ml×3). The organic phase collected was dried with anhydrous sodium sulfate, filtrated, and then condensed. The crude extract was purified by chromatography (eluent:ethyl acetate:n-hexane=1:6) to give the adduct and the results are listed in Table 1.

TABLE 1

| Entry | Compound 40 (mol %) | Temp. (° C.) | Time (h) | Yield (%)[a] | Enantiomeric excess (ee, %)[b] |
|---|---|---|---|---|---|
| 1 | 0.5 | 0 | 6 | 99 | 98 |
| 2 | 0.5 | RT | 2 | 99 | 95 |
| 3 | 0.1 | 0 | 24 | 88 | 94 |
| 4 | 0.1 | RT | 10 | 99 | 81 |
| 5 | 0.2 | 0 | 14 | 99 | 95 |

[a]Yield after purification.
[b]Determined by Chiralcel OD-H HPLC.

The results of the addition performed at 0° C. in 0.5% of amino thiol 40 are shown in Table 1. When the time of the reaction reaches 6 hours, the yield can be 99% and the ee can be 98% (Entry 1, Table 1). When the reaction is performed at room temperature, the reaction only needs two hours and its ee can reach 95% (Entry 2, Table 1). Furthermore, if the used amount of aminothiol 40 is reduced to 0.1 mol %, the ee of the reaction for 24 hours at 0° C. still reaches 94% (Entry 3, Table 1), but the reaction at room temperature has just moderate ee, i.e. 81% (Entry 4, Table 1). If the used amount of aminothiol 40 is increased to 0.2 mol %, the time of the reaction can be reduced to 14 hours and the ee thereof can reach 95% (Entry 5, Table 1).

(ii) Asymmetric Addition of Alkyl Zinc to Aldehydes

Asymmetric addition of alkyl zinc to aldehydes was performed in the presence of Compound 40 with reference to the following Scheme 5 and its results are depicted in Table 2.

Scheme 5

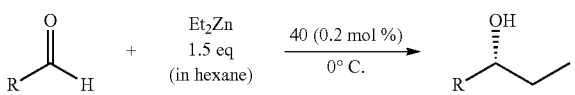

TABLE 2

| Entry | Compound | R | Time (h) | Yield (%)[a] | ee (%)[b] |
|---|---|---|---|---|---|
| 1 | 41 | Ph | 14 | 99 | 95 |
| 2 | 42 | 2-Me—Ph | 14 | 95 | 96 |
| 3 | 43 | 3-Me—Ph | 14 | 99 | 97 |
| 4 | 44 | 4-Me—Ph | 14 | 95 | 96 |
| 5 | 45 | 4-MeO—Ph | 16 | 92 | 96 |
| 6 | 46 | 4-CF$_3$—Ph | 14 | 88 | 96[c] |
| 7 | 47 | 2-Cl—Ph | 14 | 99 | 95 |
| 8 | 48 | 3-Cl—Ph | 14 | 99 | 97 |
| 9 | 49 | 4-Cl—Ph | 14 | 99 | 96 |
| 10 | 50 | 4-COOMe—Ph | 14 | 80 | 90 |
| 11 | 51 | 2-Naphthyl | 14 | 94 | 95 |
| 12 | 52 | Cinnamyl | 14 | 98 | 67 |
| 13[d] | 53 | 2-Me-cinnamyl | 24 | 96 | 96 |

[a]Yield after purification.
[b]Determined by Chiralcel OD-H and Chiralcel AD-H HPLC.
[c]Its acetate derivative determined by HPLC.
[d]Compound 40 in an amount of 1 mol %.

(ii-1) Compound 41: 1-Phenylpropanol

Compound 40 (4.3 mg, 0.01 mmol) was placed in a 10-ml dry round-bottomed flask. Diethyl zinc in n-hexane (1 M, 2.5 ml, 2.5 mmol) was added at room temperature. After 5 minutes, the mixture (1 ml) was taken out and placed in another 10-ml dry round-bottomed flask. Diethyl zinc in n-hexane (1 M, 2 ml, 2 mmol) was further added, stirred for 10 minutes at room temperature, and then cooled to 0° C. for 10 minutes. Benzaldehyde (2 mmol) was slowly added by a 250-μl airtight syringe and stirred for 14 hours. NH$_4$Cl aqueous solution (1 N, 1 ml) was added to cease reaction and 1 N HCl aqueous solution was added for neutralization (pH=7). The organic and water phases were separated and the water phase was extracted with dichloromethane (20 ml×3). The organic phase collected was dried with anhydrous sodium sulfate, filtrated, and then condensed. The crude extract was purified by chromatography (eluent:ethyl acetate:n-hexane=1:6) to give the adduct.
$^1$H-NMR (400 MHz, CDCl$_3$): δ 7.35-7.26 (m, 5H), 4.53 (t, J=6.8 Hz, 1H), 2.46 (br, 1H), 1.81-1.69 (m, 2H), 0.89 (t, J=7.6 Hz, 3H).
$^{13}$C-NMR (100 MHz, CDCl$_3$): δ 144.5 (C), 128.3 (CH), 127.3 (CH), 125.9 (CH), 75.8 (CH), 31.7 (CH$_2$), 10.1 (CH$_3$)° C.
HPLC analysis:
Column: Chiralcel OD-H.
Eluent: hexane/2-propanol (98/2).
Flow rate: 1.0 mL/min.
Retention time (t$_R$ of R-form isomer): 13.09 min.
Retention time (t$_R$ of S-form isomer): 14.46 min.
R: S=99.0: 1.0.
ee: 98%.

(ii-2) Compound 42: 1-(2-Methyphenyl)-propan-1-ol

The preparation accorded with the manner of (ii-1) except benzaldehyde used in (ii-1) was substituted by 2-methylbenzaldehyde.
$^1$H-NMR (400 MHz, CDCl$_3$): δ 7.45 (d, J=8.8 Hz, 1H), 7.25-7.12 (m, 3H), 4.83 (t, J=6.4 Hz, 1H), 2.33 (s, 3H), 2.09 (br, 1H), 1.78-1.71 (m, 2H), 0.97 (t, J=7.6 Hz, 1H).
$^{13}$C-NMR (100 MHz, CDCl$_3$): δ 142.7 (C), 134.5 (C), 130.2 (CH), 127.0 (CH), 126.1 (CH), 125.1 (CH), 71.9 (CH), 30.8 (CH$_2$), 19.0 (CH$_3$), 10.3 (CH$_3$).
HPLC analysis:
Column: Chiralcel AD-H.
Eluent: hexane/2-propanol (99/1).
Flow rate: 1.0 mL/min.
Retention time (t$_R$ of R-form isomer): 16.91 min.
Retention time (t$_R$ of S-form isomer): 20.22 min.
R: S=97.6: 2.4.
ee: 95%.

(ii-3) Compound 43: 1-(3-Methyphenyl)-propan-1-ol

The preparation accorded with the manner of (ii-1) except benzaldehyde used in (ii-1) was substituted by 3-methylbenzaldehyde.
$^1$H-NMR (400 MHz, CDCl$_3$): δ 7.24-7.07 (m, 4H), 4.51 (t, J=6.4 Hz, 1H), 2.35 (s, 3H), 2.23 (br, 1H), 1.81-1.70 (m, 2H), 0.90 (t, J=7.2 Hz, 3H).
$^{13}$C-NMR (100 MHz, CDCl$_3$): δ 144.5 (C), 137.9 (C), 128.2 (CH), 128.1 (CH), 126.6 (CH), 123.0 (CH), 75.9 (CH), 31.7 (CH$_2$), 21.4 (CH$_3$), 10.1 (CH$_3$).
HPLC analysis:
Column: Chiralcel OD-H.
Eluent: hexane/2-propanol (99/1).
Flow rate: 1.0 mL/min.
Retention time (t$_R$ of R-form isomer): 15.16 min.
Retention time (t$_R$ of S-form isomer): 21.93 min.
R: S=98.4: 1.6.
ee: 97%.

(ii-4) Compound 44: 1-(4-Methyphenyl)-propan-1-ol

The preparation accorded with the manner of (ii-1) except benzaldehyde used in (ii-1) was substituted by 4-methylbenzaldehyde.
$^1$H-NMR (400 MHz, CDCl$_3$): δ 7.21 (d, J=8.0 Hz, 2H), 7.15 (d, J=8.0 Hz, 2H), 4.52 (t, J=6.4 Hz, 1H), 2.34 (s, 3H), 2.09 (br, 1H), 1.84-1.69 (m, 2H), 0.89 (t, J=7.6 Hz, 3H).
$^{13}$C-NMR (100 MHz, CDCl$_3$): δ 141.6 (C), 137.0 (C), 129.0 (CH), 125.9 (CH), 75.8 (CH), 31.7 (CH$_2$), 21.0 (CH$_3$), 10.1 (CH$_3$).
HPLC analysis:
Column: Chiralcel OD-H.
Eluent: hexane/2-propanol (99/1).
Flow rate: 1.0 mL/min.
Retention time (t$_R$ of R-form isomer): 23.22 min.
Retention time (t$_R$ of S-form isomer): 27.47 min.
R: S=98.1: 1.9.
ee: 96%.

(ii-5) Compound 45: 1-(4-Methoxyphenyl)-propan-1-ol

The preparation accorded with the manner of (ii-1) except benzaldehyde used in (ii-1) was substituted by 4-methoxybenzaldehyde and the reaction was performed for 16 hours.
$^1$H-NMR (400 MHz, CDCl$_3$): δ 7.24 (d, J=8.4 Hz, 2H), 6.86 (d, J=8.4 Hz, 2H), 4.51 (t, J=6.4 Hz, 1H), 3.78 (s, 3H), 1.89 (br, 1H), 1.81-1.62 (m, 2H), 0.87 (t, J=7.2 Hz, 3H).
$^{13}$C-NMR (100 MHz, CDCl$_3$): δ 158.8 (C), 136.7 (C), 127.1 (CH), 113.6 (CH), 75.5 (CH), 55.1 (CH$_3$), 31.7 (CH$_2$), 10.1 (CH$_3$).

HPLC analysis:
Column: Chiralcel OD-H.
Eluent: hexane/2-propanol (98/2).
Flow rate: 1.0 mL/min.
Retention time ($t_R$ of R-form isomer): 18.91 min.
Retention time ($t_R$ of S-form isomer): 22.03 min.
R: S=98.1: 1.9.
ee: 96%.

(ii-6) Compound 46: Acetic acid 1-(4-trifluoromethyl-phenyl)-propyl ester

The preparation accorded with the manner of (ii-1) except benzaldehyde used in (ii-1) was substituted by 4-trifluromethyl-benzaldehyde.
$^1$H-NMR (400 MHz, CDCl3): δ 7.58 (d, J=8.4 Hz, 2H), 7.41 (d, J=8.0 Hz, 2H), 5.67 (t, J=6.8 Hz, 1H), 2.07 (s, 3H), 1.94-1.76 (m, 2H), 0.87 (t, J=7.2 Hz, 3H).
$^{13}$C-NMR (100 MHz, CDCl3): δ 170.2 (C), 144.6 (C), 129.9 (q, J=32.3 Hz, C), 128.1 (CH), 125.3 (q, J=3.7 Hz, CH), 122.7 (C), 76.5 (CH), 29.2 (CH2), 20.9 (CH3), 9.6 (CH3).
HPLC analysis:
Column: Chiralcel OD-H.
Eluent: hexane/2-propanol (200/1).
Flow rate: 0.5 mL/min.
Retention time ($t_R$ of S-form isomer): 10.74 min.
Retention time ($t_R$ of R-form isomer): 12.10 min.
R: S=97.8: 2.2.
ee: 96%.

(ii-7) Compound 47: 1-(2-Chlorophenyl)-propan-1-ol

The preparation accorded with the manner of (ii-1) except benzaldehyde used in (ii-1) was substituted by 2-chloro-benzaldehyde.
$^1$H-NMR (400 MHz, CDCl$_3$): δ 7.52-7.49 (m, 1H), 7.30-7.14 (m, 3H), 5.03 (t, J=6.4 Hz, 1H), 2.30 (br, 1H), 1.81-1.66 (m, 2H), 0.96 (t, J=7.6 Hz, 3H).
$^{13}$C-NMR (100 MHz, CDCl$_3$): δ 142.0 (C), 131.9 (C), 129.3 (CH), 128.3 (CH), 127.1 (CH), 126.9 (CH), 71.8 (CH), 30.4 (CH$_2$), 10.0 (CH$_3$).
HPLC analysis:
Column: Chiralcel AD-H.
Eluent: hexane/2-propanol (100/1).
Flow rate: 0.8 mL/min.
Retention time ($t_R$ of S-form isomer): 24.00 min.
Retention time ($t_R$ of R-form isomer): 25.09 min.
R: S=97.4: 2.6.
ee: 95%.

(ii-8) Compound 48: 1-(3-Chlorophenyl)-propan-1-ol

The preparation accorded with the manner of (ii-1) except benzaldehyde used in (ii-1) was substituted by 3-trifluromethyl-benzaldehyde.
$^1$H-NMR (400 MHz, CDCl$_3$): δ 7.31-7.15 (m, 4H), 4.53 (t, J=6.4 Hz, 1H), 2.15 (br, 1H), 1.79-1.69 (m, 2H), 0.88 (t, J=7.6 Hz, 3H).
$^{13}$C-NMR (100 MHz, CDCl$_3$): δ 146.6 (C), 134.2 (C), 129.6 (CH), 127.5 (CH), 126.1 (CH), 124.1 (CH), 75.2 (CH), 31.8 (CH$_2$), 9.9 (CH$_3$).
HPLC analysis:
Column: Chiralcel OD-H.
Eluent: hexane/2-propanol (99/1).
Flow rate: 1.0 mL/min.
Retention time ($t_R$ of S-form isomer): 17.96 min.
Retention time ($t_R$ of R-form isomer): 19.07 min.
R: S=98.7: 1.3.
ee: 97%.

(ii-9) Compound 49: 1-(4-Chlorophenyl)-propan-1-ol

Compound 40 (1.7 mg, 0.004 mmol) and 4-chloro-benzaldehyde (2 mmol) were placed in a 10-ml dry round-bottomed flask, cooled to 0° C., and stirred for 10 minutes. Diethyl zinc in n-hexane (1 M, 3 ml, 3 mmol) was added along the inner wall of the flask and stirred for 14 hours. NH$_4$Cl aqueous solution (1 N, 1 ml) was added to cease reaction and 1 N HCl aqueous solution was added for neutralization (pH=7). The organic and water phases were separated and the water phase was extracted with dichloromethane (20 ml×3). The organic phase collected was dried with anhydrous sodium sulfate, filtrated, and then condensed. The crude extract was purified by chromatography (eluent:ethyl acetate:n-hexane=1:6) to give the adduct.
$^1$H-NMR (400 MHz, CDCl$_3$): δ 7.27 (d, J=8.4 Hz, 2H), 7.20 (d, J=8.4 Hz, 2H), 4.50 (t, J=6.8 Hz, 1H), 2.39 (br, 1H), 1.79-1.60 (m, 2H), 0.85 (t, J=7.6 Hz, 3H).
$^{13}$C-NMR (100 MHz, CDCl$_3$): δ 142.9 (C), 132.9 (C), 128.4 (CH), 127.3 (CH), 75.1 (CH), 31.8 (CH$_2$), 9.9 (CH$_3$).
HPLC analysis:
Column: Chiralcel OD-H.
Eluent: hexane/2-propanol (99/1).
Flow rate: 1.0 mL/min.
Retention time ($t_R$ of S-form isomer): 17.34 min.
Retention time ($t_R$ of R-form isomer): 18.38 min.
R: S=98.0: 2.0.
ee: 96%.

(ii-10) Compound 50: 4-(1-Hydroxyl-propyl)-benzoic acid methyl ester

The preparation accorded with the manner of (ii-9) except 4-chloro-benzaldehyde used in (ii-9) was substituted by methyl 4-formyl benzoate.
$^1$H-NMR (400 MHz, CDCl$_3$): δ 7.91 (d, J=8.0 Hz, 2H), 7.33 (d, J=8.4 Hz, 2H), 4.58 (t, J=6.4 Hz, 1H), 3.84 (s, 3H), 2.70 (br, 1H), 1.78-1.65 (m, 2H), 0.85 (t, J=7.6 Hz, 3H).
$^{13}$C-NMR (100 MHz, CDCl$_3$): δ 167.0 (C), 149.8 (C), 129.6 (CH), 128.9 (C), 125.8 (CH), 75.2 (CH), 52.0 (CH$_3$), 31.8 (CH$_2$), 9.8 (CH$_3$).
HPLC analysis:
Column: Chiralcel AD-H.
Eluent: hexane/2-propanol (95/5).
Flow rate: 1.0 mL/min.
Retention time ($t_R$ of R-form isomer): 28.58 min.
Retention time ($t_R$ of S-form isomer): 32.19 min.
R: S=95.1: 4.9.
ee: 90%.

(ii-11) Compound 51: 1-(2-Naphthyl)propanol

The preparation accorded with the manner of (ii-1) except benzaldehyde used in (ii-1) was substituted by 2-naphthyl-benzaldehyde.
$^1$H-NMR (400 MHz, CDCl$_3$): δ 7.84-7.80 (m, 3H), 7.73 (s, 1H), 7.49-7.44 (m, 3H), 4.70 (t, J=6.4 Hz, 1H), 2.45 (br, 1H), 1.90-1.81 (m, 2H), 0.93 (t, J=7.2 Hz, 3H).
$^{13}$C-NMR (100 MHz, CDCl$_3$): δ 141.9 (C), 133.2 (C), 132.9 (C), 128.1 (CH), 127.8 (CH), 127.6 (CH), 126.0 (CH), 125.6 (CH), 124.6 (CH), 124.1 (CH), 75.9 (CH), 31.6 (CH$_2$), 10.1 (CH$_3$).

HPLC analysis:
Column: Chiralcel OD-H.
Eluent: hexane/2-propanol (98/2).
Flow rate: 1.0 mL/min.
Retention time ($t_R$ of S-form isomer): 29.61 min.
Retention time ($t_R$ of R-form isomer): 33.66 min.
R: S=97.9: 2.1.
ee: 96%.

(ii-12) Compound 52: (E)-1-phenylpent-1-en-3-ol

The preparation accorded with the manner of (ii-1) except benzaldehyde used in (ii-1) was substituted by cinnamaldehyde.

$^1$H-NMR (400 MHz, CDCl$_3$): δ 7.38-7.20 (m, 5H), 6.56 (d, J=16.0 Hz, 1H), 6.20 (dd, J=15.6 Hz, 6.8 Hz, 1H), 4.19 (m, 1H), 1.96 (br, 1H), 1.69-1.60 (m, 3H), 0.96 (t, J=7.2 Hz, 3H).
$^{13}$C-NMR (100 MHz, CDCl$_3$): δ 136.7 (C), 132.2 (CH), 130.3 (CH), 128.5 (CH), 127.5 (CH), 126.4 (CH), 74.3 (CH), 30.1 (CH$_2$), 9.7 (CH$_3$).
HPLC analysis:
Column: Chiralcel OD-H.
Eluent: hexane/2-propanol (90/10).
Flow rate: 1.0 mL/min.
Retention time ($t_R$ of R-form isomer): 6.82 min.
Retention time ($t_R$ of S-form isomer): 9.45 min.
R: S=83.4: 16.6.
ee: 67%.

(ii-13) Compound 53: (E)-2-Methyl-1-phenylpent-1-en-3-ol

The preparation accorded with the manner of (ii-1) except benzaldehyde used in (ii-1) was substituted by α-methyl cinnamaldehyde and the used amount of Compound 40 was 1 mol %.

$^1$H-NMR (400 MHz, CDCl3): δ 7.35-7.26 (m, 4H), 7.24-7.19 (m, 1H), 6.48 (s, 1H), 4.09 (t, J=6.6 Hz, 1H), 2.06 (br, 1H), 1.85 (s, 3H), 1.67 (m, 2H), 0.94 (t, J=7.2 Hz, 3H).
$^{13}$C-NMR (100 MHz, CDCl$_3$): δ140.0 (C), 137.5 (C), 128.9 (CH), 128.0 (CH), 126.3 (CH), 125.9 (CH), 79.4 (CH), 27.9 (CH$_2$), 13.0 (CH$_3$), 10.0 (CH$_3$).
HPLC analysis:
Column: Chiralcel OD-H.
Eluent: hexane/2-propanol (99/1).
Flow rate: 1.0 mL/min.
Retention time ($t_R$ of R-form isomer): 21.25 min.
Retention time ($t_R$ of S-form isomer): 24.27 min.
R: S=98.2: 1.8.
ee: 96%.

Applicant Example 2

Asymmetric Addition of Aryl Zinc to Various Aldehydes

With reference to the following Scheme 6, it shows asymmetric addition to various aldehydes in the presence of Compound 40 and its results are shown in Table 3.

Scheme 6

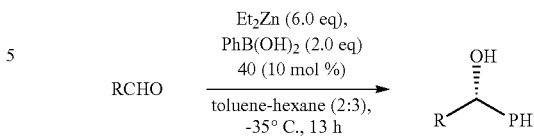

TABLE 3

| Entry | Compound | R | Yield (%)$^a$ | ee (%)$^b$ |
|---|---|---|---|---|
| 1 | 54 | 4-Me—Ph | 95 | 97 |
| 2 | 55 | 4-COOMe—Ph | 98 | 89 |
| 3 | 56 | 2-Naphthyl | 90 | 95 |

$^a$Yield after purification.
$^b$Determined by Chiralcel OD-H HPLC.

(i-1) Compound 54: Phenyl-p-tolyl-methanol

Phenyl boric acid (122 mg, 1.0 mmol) was placed in a 10-ml dry two-necked flask and the flask was equipped with a reflux tube under an atmosphere of argon. Methylbenzene (2 ml) and diethyl zinc in hexane (1 M, 3 ml, 3 mmol) was added in the flask in sequence. The mixture was heated to 60° C. for 12 hours and then cooled to room temperature. Compound 40 (21.6 mg, 0.05 mmol) was placed in another 10-ml dry round-bottomed flask under an atmosphere of argon and the mixture was added in the round-bottomed flask. The mixture was stirred at room temperature for 10 hours and then cooled to –35° C. for 10 minutes, and 4-methyl-benzaldehyde (0.5 mmol) was slowly added by a 100-μl airtight syringe. After the reaction was performed for 13 hours, saturated NH$_4$Cl aqueous solution (5 ml) was added to stop the reaction. The mixture was extracted with dichloromethane (25 ml×3), dried with anhydrous sodium sulfate, filtrated, and condensed. The obtained crude extract was purified by chromatography (eluent:ethyl acetate:n-hexane 1:6) to afford the adduct.

$^1$H-NMR (400 MHz, CDCl$_3$): δ 7.39-7.33 (m, 4H), 7.30-7.26 (m, 3H), 7.16 (d, J=7.6 Hz, 2H), 5.77 (s, 1H), 2.52 (br, 1H), 2.36 (s, 3H).
$^{13}$C-NMR (100 MHz, CDCl$_3$): δ 143.9 (C), 140.9 (C), 137.1 (C), 129.1 (CH), 128.3 (CH), 127.3 (CH), 126.5 (CH), 126.4 (CH), 75.9 (CH), 21.0 (CH$_3$).
HPLC analysis:
Column: Chiralcel OD-H.
Eluent: hexane/2-propanol (98/2).
Flow rate: 1.0 mL/min.
Retention time ($t_R$ of S-form isomer): 24.53 min.
Retention time ($t_R$ of R-form isomer): 28.00 min.
R: S=98.4: 1.6.
ee: 97%.

(i-2) Compound 55: 4-(Hydroxyl-phenyl-methyl)-benzoic acid methyl ester

Phenyl boric acid (122 mg, 1.0 mmol) was placed in a 10-ml dry two-necked flask and the flask was equipped with a reflux tube under an atmosphere of argon. Methylbenzene (2 ml) and diethyl zinc in hexane (1 M, 3 ml, 3 mmol) was added in the flask in sequence. The mixture was heated to 60° C. for 12 hours and then cooled to room temperature. Compound 40 (21.6 mg, 0.05 mmol) and methyl 2-formylbenzoate (0.5 mmol) were placed in another 10-ml dry round-bottomed flask under an atmosphere of argon, cooled to −35° C., and then stirred for 10 minutes. The mixture was slowly added along the inner wall in the round-bottomed flask. After the reaction was performed for 13 hours, saturated NH$_4$Cl aqueous solution (5 ml) was added to stop the reaction. The mixture was extracted with dichloromethane (25 ml×3), dried with anhydrous sodium sulfate, filtrated, and condensed. The obtained crude extract was purified by chromatography (eluent:ethyl acetate:n-hexane=1:6) to afford the adduct.

$^1$H-NMR (400 MHz, CDCl$_3$): δ 7.97 (d, J=8.4 Hz, 2H), 7.44 (d, J=8.0 Hz, 2H), 7.33-7.26 (m, 5H), 5.85 (s, 1H), 3.87 (s, 3H), 2.50 (br, 1H).

$^{13}$C-NMR (100 MHz, CDCl$_3$): δ 166.9 (C), 148.8 (C), 143.2 (C), 129.7 (CH), 129.1 (C), 128.6 (CH), 127.8 (CH), 126.6 (CH), 126.3 (CH), 75.8 (CH), 52.0 (CH$_3$).

HPLC analysis:
Column: Chiralcel OD-H.
Eluent: hexane/2-propanol (90/10).
Flow rate: 0.5 mL/min.
Retention time (t$_R$ of R-form isomer): 33.35 min.
Retention time (t$_R$ of S-form isomer): 38.83 min.
R: S=94.5: 5.5.
ee: 89%.

(i-3) Compound 56:
Naphthalen-2-yl-phenyl-methanol

The preparation accorded with the manner of (i-1) except 4-methyl benzaldehyde used in (i-1) was substituted by 2-naphthyl-benzaldehyde.

$^1$H-NMR (400 MHz, CDCl$_3$): δ 7.89-7.77 (m, 41-1), 7.48-7.25 (m, 8H), 6.00 (s, 1H), 2.34 (br, 1H).

$^{13}$C-NMR (100 MHz, CDCl$_3$): δ 143.6 (C), 141.1 (C), 133.2 (C), 132.8 (C), 128.4 (CH), 128.2 (CH), 128.0 (CH), 127.6 (CH), 127.6 (CH), 126.6 (CH), 126.1 (CH), 125.9 (CH), 125.0 (CH), 124.7 (CH), 76.2 (CH).

HPLC analysis:
Column: Chiralcel OD-H.
Eluent: hexane/2-propanol (90/10).
Flow rate: 0.5 mL/min.
Retention time (t$_R$ of S-form isomer): 29.78 min.
Retention time (t$_R$ of R-form isomer): 34.99 min.
R: S=97.3: 2.7.
ee: 95%.

Application Example 3

Asymmetric Addition of Diethyl Zinc to Aldehydes (i) Asymmetric Addition to β-Amino Alcohol 34 Catalyzed at Various Temperatures With reference to the following Scheme 6, it shows addition of ethyl in diethyl zinc to benzaldehyde in the presence of β-amino alcohol 34 used as a chiral ligand.

Scheme 6

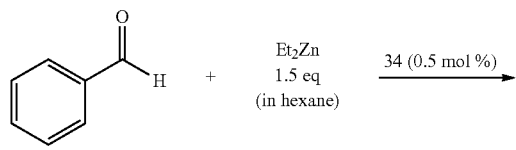

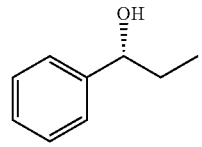

Compound 34 (0.5 mol %) and benzaldehyde (2 mmol) were placed in a 10-ml dry round-bottomed flask. The mixture was adjusted to the predetermined temperatures (Table 4) and stirred for 10 minutes. Subsequently, diethyl zinc in hexane (1 M, 3 ml, 3 mmol) was added along the inner wall in the round-bottomed flask. The mixture was stirred for several hours. Saturated NH$_4$Cl aqueous solution (5 ml) was added to stop the reaction and 1 N HCl aqueous solution was added for neutralization (pH=7). The water and organic phases were separated and the water phase was extracted with dichloromethane (20 ml×3). The organic phase collected was dried with anhydrous sodium sulfate, filtrated, and condensed. The obtained crude extract was purified by chromatography (eluent:ethyl acetate:n-hexane=1:6) to afford the adduct and the result is shown in Table 4.

TABLE 4

| Entry | Temp. (° C.) | Time (h) | Yield (%)$^a$ | ee (%)$^b$ |
|---|---|---|---|---|
| 1 | 0 | 24 | 89 | 92 |
| 2 | RT | 12 | 84 | 82 |

$^a$Yield after purification.
$^b$Determined by Chiralcel OD-H HPLC.

As shown in Table 4, the addition of diethyl zinc in n-hexane performed at 0° C. in presence of β-amino alcohol 34 (0.5 mol %) for 24 hours can give 92% ee (Entry 1, Table 4). Even though the reaction was performed at room temperature, 82% ee still can be given (Entry 2, Table 4).

In conclusion, the camphor-derived compounds of the present invention can be used as novel chiral ligands. Furthermore, asymmetric addition of diethyl zinc to aldehydes can be performed at 0° C. in the presence of β-amino thiol 40 only in amount of 0.2 mol % and then give 80-99% yield and 97% ee (the most). Besides, when asymmetric addition of aryl to aldehydes was performed for 13 hours in the presence of amino thiol 40, the reaction gave 90-98% yield and 89-97% ee. This demonstrates the champhor-derived compounds of the present invention can give desirable potential in an application of synthesis and in consideration of economic costs.

Although the present invention has been explained in relation to its preferred embodiment, it is to be understood that many other possible modifications and variations can be made without departing from the scope of the invention as hereinafter claimed.

What is claimed is:

1. A camphor-derived compound as represented in the following formula (I):

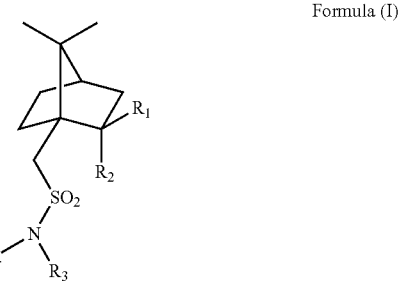

Formula (I)

wherein $R_1$ and $R_2$ independently are $-OR_a$, $-SR_b$, or

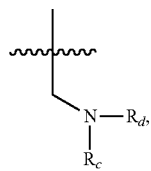

and when $R_1$ is $-OR_a$ or $SR_b$, $R_2$ is

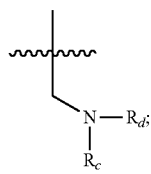

when $R_1$ is

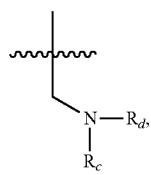

$R_2$ is $-OR_a$ or $SR_b$, wherein $R_a$ is H or silyl substituted by one to three $C_{1-10}$ alkyl, $R_b$ is H or $C_{1-10}$ alkyl substituted by $C_{6-14}$ aryl, $R_c$ and $R_d$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_c$ and $R_d$ are conjugated to form $-(CH_2)_m Z(CH_2)_n-$, wherein m and n are 1, 2, or 3, Z is $-CH_2-$, $-NH-$, $-O-$, or $-S-$; and $R_3$ and $R_4$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_3$ and $R_4$ are conjugated to form $-(CH_2)_m Z(CH_2)_n-$, wherein m and n are 1, 2, or 3, Z is $-CH_2-$, $-NH-$, $-O-$, or $-S-$.

2. The camphor-derived compound as claimed in claim 1, wherein $R_1$ is thiol or hydroxyl.

3. The camphor-derived compound as claimed in claim 2, wherein $R_2$ is

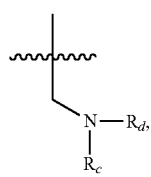

wherein $R_c$ and $R_d$ are conjugated to form $-(CH_2)_m Z(CH_2)_n-$.

4. The camphor-derived compound as claimed in claim 3, wherein Z is $-O-$ and a sum of m and n is 3 or 4.

5. The camphor-derived compound as claimed in claim 4, wherein $R_3$ and $R_4$ independently are $C_{1-10}$ alkyl.

6. The camphor-derived compound as claimed in claim 1, wherein $R_2$ is thiol or hydroxyl.

7. The camphor-derived compound as claimed in claim 6, wherein $R_1$ is

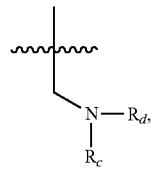

wherein $R_c$ and $R_d$ are conjugated to form $-(CH_2)_m Z(CH_2)_n-$.

8. The camphor-derived compound as claimed in claim 7, wherein Z is $-O-$ and a sum of m and n is 3 or 4.

9. The camphor-derived compound as claimed in claim 8, wherein $R_3$ and $R_4$ independently are $C_{1-10}$ alkyl.

10. A method for manufacturing a camphor-derived compound, comprising the following steps:
(a) providing a compound represented by the following formula (Ia), Formula (Ia)

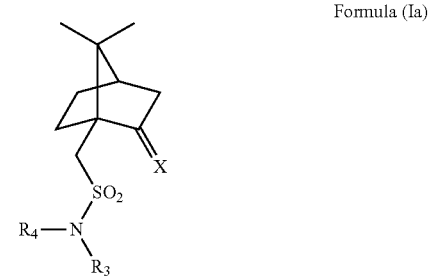

wherein X is O, or S, $R_3$ and $R_4$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_3$ and $R_4$ are conjugated to form $-(CH_2)_m Z(CH_2)_n-$, wherein m and n are 1, 2, or 3, Z is $-CH_2-$, $-NH-$, $-O-$, or $-S-$; and (b) forming a compound represented by the following formula (I) from the compound represented by the formula (Ia), Formula (I)

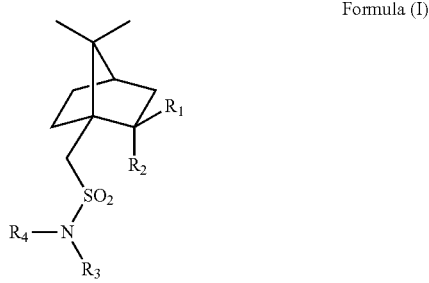

wherein $R_1$ and $R_2$ independently are $-OR_a$, $-SR_b$, cyano, $-CH_2NH_2$, or

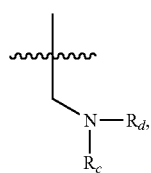

and when $R_1$ is —$OR_a$ or $SR_b$, $R_2$ is cyano, —$CH_2NH_2$, or

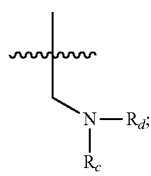

when $R_1$ is cyano, —$CH_2NH_2$, or

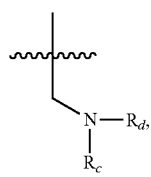

$R_2$ is —$OR_a$ or $SR_b$, wherein $R_a$ is H or silyl substituted by one to three $C_{1-10}$ alkyl, $R_b$ is H or $C_{1-10}$ alkyl substituted by $C_{6-14}$ aryl, $R_c$ and $R_d$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_c$ and $R_d$ are conjugated to form —$(CH_2)_m Z(CH_2)_n$—, wherein m and n are 1, 2, or 3, Z is —$CH_2$—, —NH—, —O—, or —S—; or $R_1$ and $R_2$ are combined to form =O, or =S.

11. The method as claimed in claim 10, wherein in the step (a) the compound of the formula (Ia) in which X is S, is formed by reacting the compound of the formula (Ia) in which S is O with a Lawesson's reagent.

12. The method as claimed in claim 11, wherein in the step (b) the compound of the formula, (I) in which $R_1$ and $R_2$ independently are benzylthiol and cyano, is formed by reacting benzyl halide with the compound of formula (I) in which $R_1$ and $R_2$ independently are thiol and cyano formed after the compound of the formula (Ia) in which X is S, is reacted with silyl cyanide.

13. The method as claimed in claim 12, wherein the compound of the formula (I) in which $R_1$ and $R_2$ independently are benzylthiol and cyano, is reduced to form the compound of the formula (I) in which $R_1$ is benzylthiol and $R_2$ is —$CH_2NH_2$, followed by N-alkylation with $W_1$—$(CH_2)_m Z(CH_2)_n$—$W_2$ to form the compound of the formula (I) in which $R_2$ is

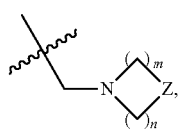

wherein $W_1$ and $W_2$ are leaving groups.

14. The method as claimed in claim 13, wherein the compound of the formula (I) in which $R_1$ is benzythiol, is reduced to form the compound of the formula (I) in which $R_1$ is thiol.

15. The method as claimed in claim 10, wherein in the step (b) the compound of formula (I) in which $R_1$ and $R_2$ independently are silyloxy and cyano formed after the compound of the formula (Ia) in which X is O, is reacted with silyl cyanide, is reduced to form the compound of the formula (I) in which $R_1$ and $R_2$ independently are hydroxyl and —$CH_2NH_2$, followed by N-alkylation with $W_1$—$(CH_2)_m Z(CH_2)_n$—$W_2$ to form the compound of the formula (I) in which $R_2$ is

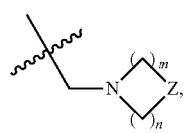

wherein $W_1$ and $W_2$ are leaving groups.

16. The method as claimed in claim 10, wherein in the step (b), the compound of the formula (I) in which $R_1$ and $R_2$ independently are hydroxyl and

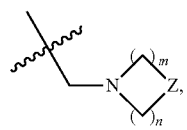

is formed by reacting the compound of the formula (Ia) in which X is S with

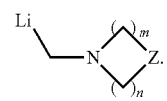

17. A method for asymmetric addition of an organic zinc to an aldehyde, comprising the following step: reacting $R_5C(O)H$ and $R_6ZnR_7$ in presence of a catalyst represented by the following formula (I), Formula (I)

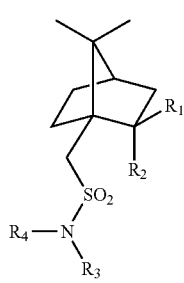

wherein $R_1$ and $R_2$ independently are —$OR_a$, —$SR_b$, cyano, —$CH_2NH_2$, or

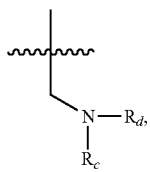

and when $R_1$ is —$OR_a$ or $SR_b$, $R_2$ is cyano, —$C_2H_2$, or

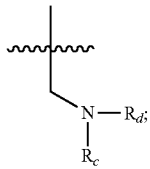

when $R_1$ is cyano, —$CH_2NH_2$, or

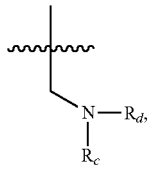

$R_2$ is —$OR_a$ or $SR_b$, wherein $R_a$ is H or silyl substituted by one to three $C_{1-10}$ alkyl, $R_b$ is H or $C_{1-10}$ alkyl substituted by $C_{6-14}$ aryl, $R_c$ and $R_d$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_c$ and $R_d$ are conjugated to form —$(CH_2)_m Z(CH_2)_n$—, wherein m and n are 1, 2, or 3, Z is —$CH_2$—, NH—, —O—, or —S—; or $R_1$ and $R_2$ are combined to form =O, or =S; and $R_3$ and $R_4$ independently are $C_{1-10}$ alkyl, $C_{5-14}$ cycloalkyl, $C_{4-13}$ heterocycloalkyl, $C_{6-14}$ aryl, or $C_{4-13}$ heteroaryl, wherein the heterocyclo and the heteroaryl have at least one heteroatom selected from the group consisting of O, S, Se, and N, or $R_3$ and $R_4$ are conjugated to form —$(CH_2)_m Z(CH_2)_n$—, wherein m and n are 1, 2, or 3, Z is —$CH_2$—, —NH—, —O—, or —S—; and $R_5$, $R_6$ and $R_7$ independently are $C_{1-10}$ alkyl, $C_{2-10}$ alkenyl, $C_{5-14}$ cycloalkyl, $C_{4-13}$ heterocycloalkyl, $C_{5-14}$ cycloalkenyl, $C_{5-14}$ heterocycloalkenyl, $C_{6-14}$ aryl, or $C_{4-13}$ heteroaryl, wherein the heterocycloalkyl, the heterocycloalkenyl and the heteroaryl have at least one heteroatom selected from the group consisting of O, S, Se, and N, wherein the $C_{1-10}$ alkyl, the $C_{2-10}$ alkenyl, the $C_{5-14}$ cycloalkyl, the $C_{4-13}$ heterocycloalkyl, the $C_{5-14}$ cycloalkenyl, the $C_{5-14}$ heterocycloalkenyl, the $C_{6-14}$ aryl, or the $C_{4-13}$ heteroaryl is optionally substituted by $C_{1-10}$ alkyl, halogen, cyano, —$CO_2$—$C_{1-10}$ alkyl, —$CO_2$—$C_{2-10}$ alkenyl, $C_{1-10}$ haloalkyl, $C_{2-10}$ alkenyl, $C_{1-10}$ alkoxyl, $C_{5-14}$ cycloalkyl, $C_{4-13}$ heterocycloalkyl, $C_{5-14}$ cycloalkenyl, $C_{5-14}$ heterocycloalkenyl, $C_{6-14}$ aryl, or $C_{4-13}$ heteroaryl.

18. The method as claimed in claim 17, wherein the catalyst of the formula (I) is used in an amount of 0.1-10 mol % based on a mole amount of the aldehyde $R_5C(O)H$.

19. The method as claimed in claim 18, wherein the organic zinc $R_6ZnR_7$ is used in an amount of 0.5-5 equivalents based on the amount of the aldehyde $R_5C(O)H$.

* * * * *